(12) United States Patent
Hadeiba et al.

(10) Patent No.: US 8,889,124 B2
(45) Date of Patent: Nov. 18, 2014

(54) TOLEROGENIC POPULATIONS OF DENDRITIC CELLS

(75) Inventors: Husein Hadeiba, Daly City, CA (US); Eugene C. Butcher, Portola Valley, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 378 days.

(21) Appl. No.: 12/566,454

(22) Filed: Sep. 24, 2009

(65) Prior Publication Data

US 2010/0080816 A1 Apr. 1, 2010

Related U.S. Application Data

(60) Provisional application No. 61/100,222, filed on Sep. 25, 2008.

(51) Int. Cl.
| | | |
|---|---|---|
| A01N 63/00 | (2006.01) | |
| A01N 1/02 | (2006.01) | |
| C12N 5/071 | (2010.01) | |
| C12N 5/0784 | (2010.01) | |
| A61K 35/12 | (2006.01) | |
| A61K 39/00 | (2006.01) | |

(52) U.S. Cl.
CPC ....... *A61K 39/0008* (2013.01); *A61K 2035/122* (2013.01); *C12N 5/064* (2013.01); *A61K 2039/5154* (2013.01)
USPC ............................. 424/93.71; 435/2; 435/372

(58) Field of Classification Search
None
See application file for complete search history.

(56) References Cited

U.S. PATENT DOCUMENTS

| 2005/0013810 A1* | 1/2005 | Waller et al. ............... 424/144.1 |
|---|---|---|
| 2006/0182726 A1* | 8/2006 | Thomas et al. ............ 424/93.21 |
| 2006/0199228 A1* | 9/2006 | Peakman ....................... 435/7.2 |

OTHER PUBLICATIONS

Papadakis et al., 2000, J. Immunol. vol. 165: 5069-5076.*
Pillarisetty et al., 2003, Hepatology, vol. 37: 641-652.*
McKenna et al., 2005, J. Virol. vol. 79: 17-27.*
Dhodapkar et al., 2001, vol. 193: 233-238.*
Yi et al., 2003, J. Immunol. vol. 170: 2750-58.*
Coombes et al., Aug. 2007, vol. 204: 1757-1764.*
Jaensson et al., Aug. 2008, J. Exp. Med. vol. 205: 2139-49.*
Zabel et al., 2005, J. Immunol. vol. 174: 244-251.*
Arpinati; et al., "Role of plasmacytoid dendritic cells in immunity and tolerance after allogeneic hematopoietic stem cell transplantation", Transplant Immunology (2003), 11:345-356.
Chen; et al., "Thrombopoietin cooperates with FLT3-ligand in the generation of plasmacytoid dendritic cell precursors from human hematopoietic progenitors", Blood (2004), 103(7):2547-2553.
Cohen; et al., "CD4+CD25+Immunoregulatory T Cells: New Therapeutics for Graft-Versus-Host Disease", J. Exp. Med. (2002), 196(3):401-406.
Gilliet; et al., "The Development of Murine Plasmacytoid Dendritic Cell Precursors is Differentially Regulated by FLT3-ligand and Granulocyte/Macrophage Colony-Stimulating Factor", J. Exp. Med. (2002), 195(7):953-958.
Hoffman; et al., "Donor-type CD4+CD25+Regulatory T Cells Suppress Lethal Acute Graft-Versus-Host Disease after Allogeneic Bone Marrow Transplantation", J. Exp. Med. (2002), 196(3):389-399.
Martin; et al., "Characterization of a new subpopulation of mouse CD8alpha+B220+dendritic cells endowed with type 1 interferon production capacity and tolerogenic potential", Blood (2002), 100(2):383-390.
Morelli; et al., "Tolerogenic dendritic cells and the quest for transplant tolerance", Nature Reviews (2007), 7:610-621.
Van Duivenvoorde; et al., "Dendritic cells: Vehicles for tolerance induction and prevention of autoimmune disease", Immunobiology (2006), 211:627-632.

* cited by examiner

*Primary Examiner* — Amy Juedes
(74) *Attorney, Agent, or Firm* — Bozicevic, Field & Francis LLP; Pamela J. Sherwood

(57) ABSTRACT

Tolerogenic populations of dendritic cells are provided, where the dendritic cells are characterized by expression of select tissue-specific homing receptors including the chemokine receptors CCR9; or CMKLR1; or the integrin CD103. The dendritic cells may be conventional/myeloid or plasmacytoid dendritic cells. The cells may be isolated from lymphoid tissue, from blood, or from in vitro culture, e.g. bone marrow culture, etc. Methods are provided for their identification, isolation and targeting in immunotherapeutic interventions in suppressing inflammatory disorders including autoimmunity, transplantation responses and allergic diseases. In some embodiments dendritic cell populations are fixed to render them immunosuppressive, thus allowing the cells to be typed and banked for future use.

5 Claims, 14 Drawing Sheets

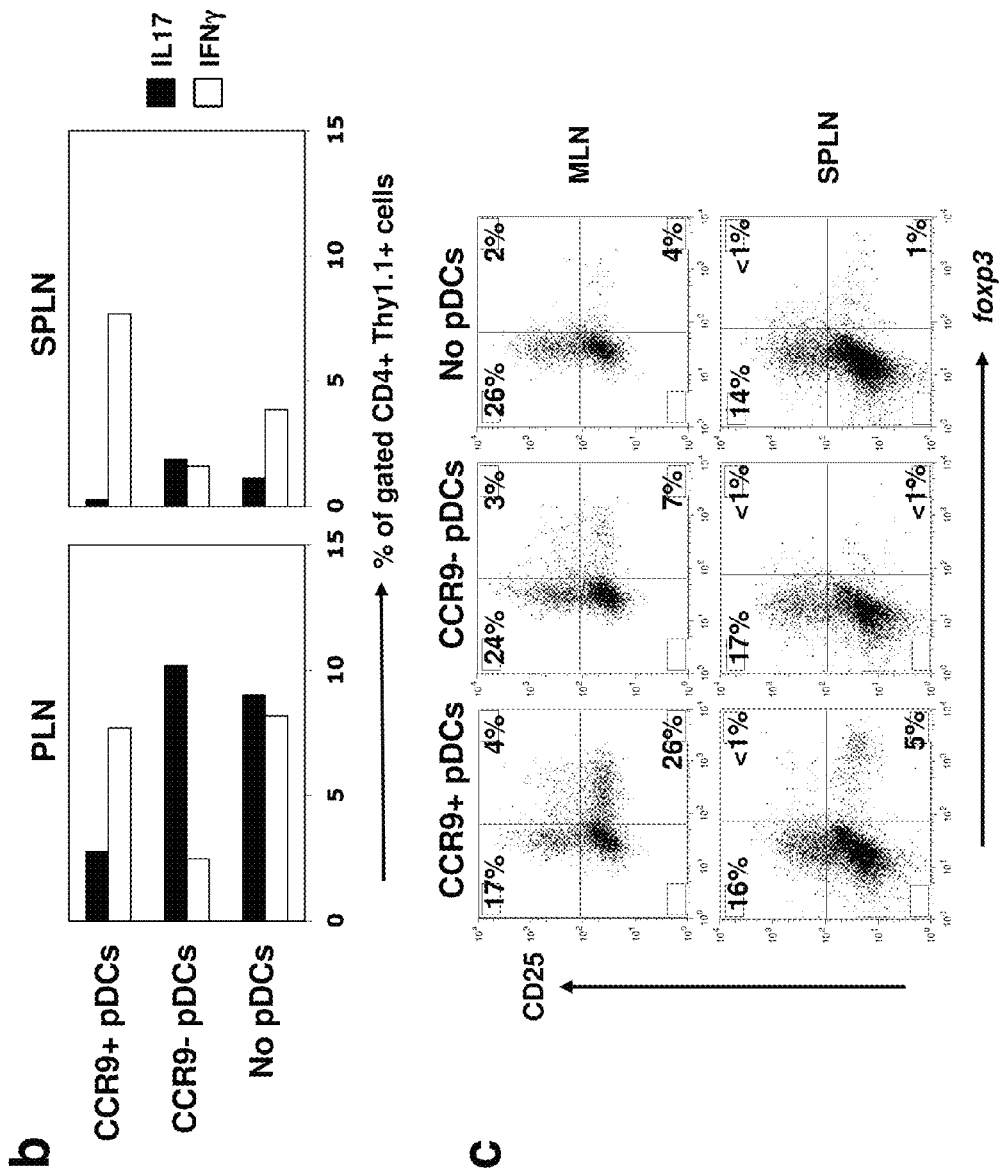
Figure 7b&c

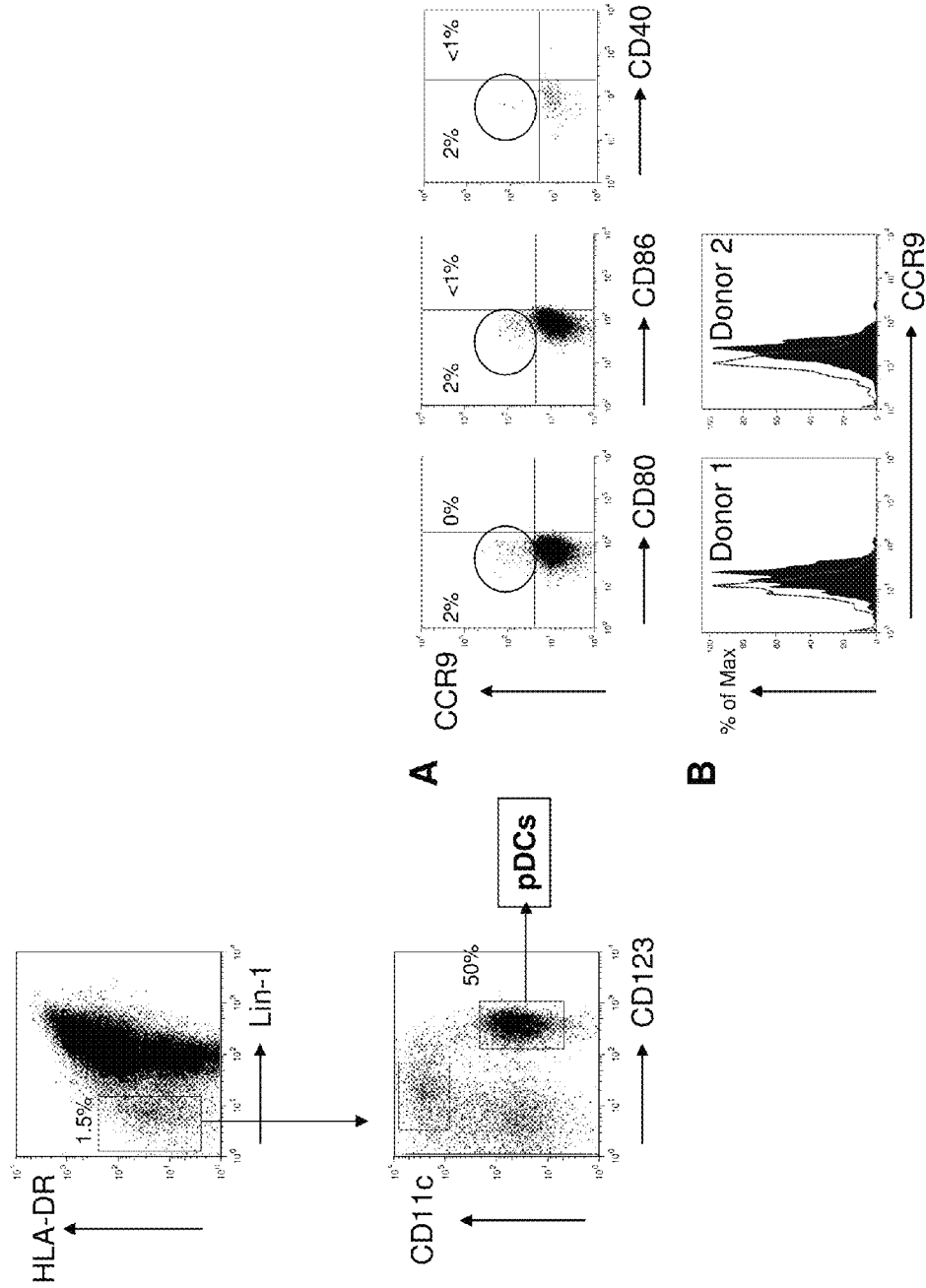
*Figure 8a&b*
Analogous CCR9+ pDCs also seen in human tonsil and flt3L-cultured bone marrow.

Cytokine responses of CD4+ T cells cultured *in-vitro* with "live" or "fixed" CD103+ cDCs.

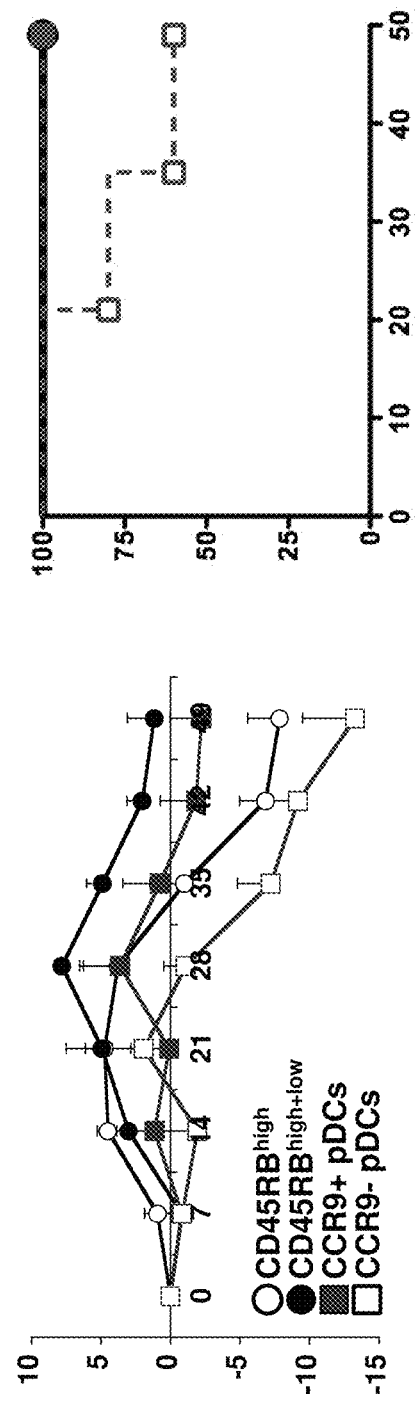
*Figure 12a&b*

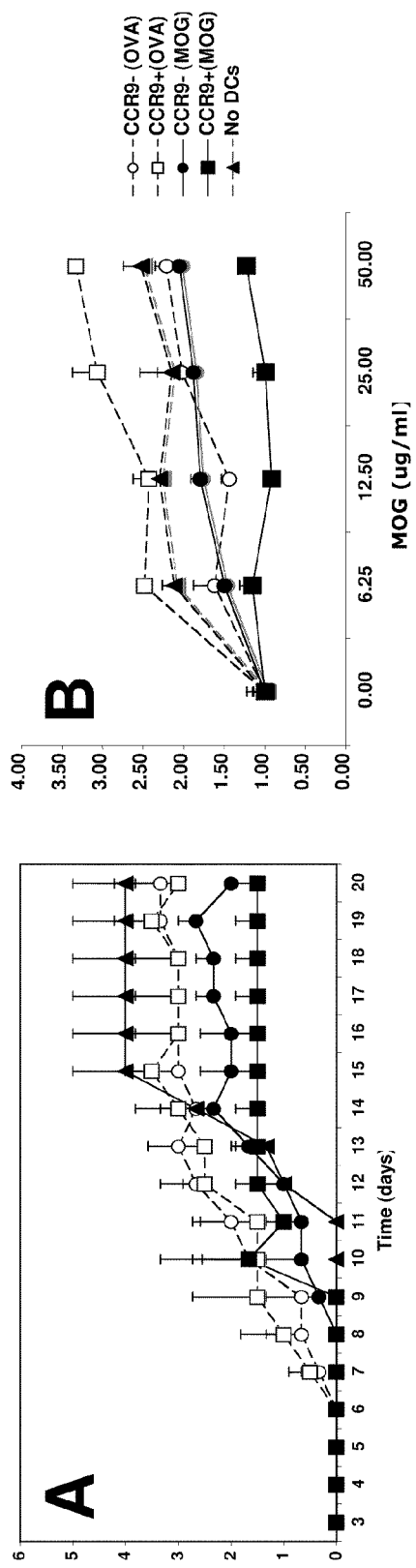
*Figure 13* Antigen-loaded CCR9+ DCs suppress clinical symptoms of EAE.

US 8,889,124 B2

TOLEROGENIC POPULATIONS OF DENDRITIC CELLS

FEDERALLY-SPONSORED RESEARCH OR DEVELOPMENT

This invention was made with Government support under contract AI007290 awarded by the National Institutes of Health. The Government has certain rights in this invention.

BACKGROUND OF THE INVENTION

The mammalian immune system provides a springboard for much of modern medicine through its ability to raise a specific response against undesirable targets in the body. However, there are other conditions where the immune response is undesirable, e.g. in transplantation, allergy and in the context of autoimmune disease. While T cells orchestrate the immune response, they do not effectively respond to antigen unless the antigen is processed and presented to them by the appropriate antigen presenting cells. The 3 major classes of antigen presenting cells are dendritic cells (DCs), macrophages, and B cells, but dendritic cells are considerably more potent on a cell-to-cell basis.

DC precursors migrate from bone marrow and circulate in the blood to specific sites in the body, where they mature. This trafficking is directed by expression of chemokine receptors and adhesion molecules. Upon exposure to antigen and activation signals, the DCs are activated, and leave tissues to migrate via the afferent lymphatics to the T cell rich paracortex of the draining lymph nodes. The activated DCs then secrete chemokines and cytokines involved in T cell homing and activation, and present processed antigen to T cells. This link between DC traffic pattern and functions has led to the investigation of the chemokine responsiveness of DCs during their development and maturation. Chemokines are a subclass of cytokines, which have distinct structural features and biological effects. Their primary activity appears to be on the chemotaxis of leukocytes. All chemokines bind to members of a G-protein coupled serpentine receptor superfamily that span the leukocyte cell surface membrane seven times (7-TM). A review of known chemokines may be found in Rossi (2000) Annual Review of Immunology 18:217-42. For a review of the effect of chemokines on DC subsets, see Dieu-Nosjean (1999) J. Leuk. Biol. 66(2):252-62.

DCs mature by upregulating costimulatory molecules (CD40, CD80 and CD86), and migrate to T cell areas of organized lymphoid tissues where they activate naive T cells and induce effector rather than tolerogenic immune responses. In the absence of such inflammatory or infectious signals, however, DCs present self-antigens in secondary lymphoid tissues for the induction and maintenance of self-tolerance. The ability of DCs to induce tolerance has led to numerous studies using these cells therapeutically in an effort to control unwanted immune responses in models of allograft rejection, graft-versus-host disease (GVHD) and autoimmune disorders. Most studies have employed myeloid DCs (mDCs) derived from mouse bone marrow or human monocytes cultured in vitro using the cytokines granulocyte-macrophage colony stimulating factor (GM-CSF) in the presence or absence of interleukin 4 (IL-4).

For example, in vitro derived immature mDCs were able to dampen arthritis in an antigen-driven mouse model or prolong allograft survival in a murine transplant model. See Martin et al. (2002) Blood 100:383-390; Hoffmann et al. (2002) J Exp Med 196:389-399; Cohen et al. (2002) J Exp Med 196:401-406; van Duivenvoorde et al. (2006) Immunobiology 211:627-632; and Morelli and Thomson (2007) Nat Rev Immunol 7:610-621. Some studies have further manipulated mDCs through genetic modification or exposure to either immunosuppressive agents, or cytokines such as IL-10 and transforming growth factor-$\beta$ (TGF-$\beta$) in an effort to generate more potent tolerogenic mDC populations. Recent studies suggest that lymphoid-related $CD11c^+$ $CD8\alpha^+$ DCs, mobilized in vivo by the hematopoietic growth factor fms-like tyrosine kinase 3 ligand (Flt3L), may prolong the survival of vascularized heart allografts in rodents.

Plasmacytoid DCs are best known for their high production amounts of type I interferons and subsequent induction of cell-mediated adaptive immune responses after viral activation, although freshly isolated pDCs, in the absence of maturation signals, do not induce strong T cell responses (see Gilliet et al. (2002) J Exp Med 195:953-958; Chen et al. (2004) Blood 103:2547-2553; Arpinati et al. (2003) Transpl Immunol 11, 345-356).

In spite of the promise of cellular therapy with DC populations, to date no studies have taken advantage of specific tolerogenic phenotypes to sort immunosuppressive from immune activating DCs. Perhaps as a consequence, most DC populations studied have yielded only partial or transient amelioration of autoimmune symptoms or allograft survival. Methods for tolerization with biologically relevant cell populations are of great scientific and clinical interest.

SUMMARY OF THE INVENTION

Compositions and methods are provided that relate to tolerogenic populations of dendritic cells, where the dendritic cells are characterized by expression of a tissue specific homing receptor. Cells of interest include immature plasmacytoid dendritic cells (pDC) expressing CCR9; immature human pDCs expressing CMKLR1; and conventional dendritic cells expressing CD103. The cells may be isolated from complex populations based on expression of CCR9; CD103; or CMKLR1, etc. In some embodiments, the dendritic cells are immature plasmacytoid dendritic cells or conventional dendritic cells. The cells may be isolated from lymphoid tissue, from blood, or from in vitro culture, e.g. monocytes or bone marrow cell culture, etc. Thus, in some embodiments the tolerogenic cells are CCR9+ immature pDC cells, e.g. from a human or a mouse donor. In other embodiments the tolerogenic cells are CMKLR1+ immature pDC cells, e.g. from a human or a mouse donor. In other embodiments, the tolerogenic cells are CD103+ conventional DC cells, e.g. from a human or a mouse donor.

The populations that are immature plasmacytoid dendritic cells may be further characterized, and optionally isolated on the basis of, expression of intermediate levels of CD11c and expression of B220 in mice. The cells are optionally selected to be CD3/CD19 negative. In humans the cells may be characterized, and optionally isolated on the basis of low levels of CD11c and high levels of CD123 (IL-3R$\alpha$ chain). The cells are optionally selected to be Lineage-1 negative cells, i.e. negative for expression of CD3, CD14, CD16, CD19, CD20, CD56. The cells have an immature phenotype, e.g. express low levels of CD40, CD80, CD83 and CD86, and express low to intermediate levels of MHC Class II antigens, for both mice and humans.

In other embodiments of the invention, the tolerogenic dendritic cells are fixed cells, i.e. cells chemically treated to kill the cells while preserving antigenic structure. The fixed tolerogenic cells are not required to express the tissue specific homing receptor, although such expression may provide advantages in certain situations, e.g. where the cells are to be localized at a site of interest. Thus in some embodiments the tolerogenic cells are fixed dendritic cells; and are optionally fixed CCR9+ pDC; CMKLR1+ pDC; CD103+ DC, which may have one or more MHC alleles that differ from an intended host; or may be pulsed with an antigen of interest prior to fixation.

In some embodiments of the invention, an isolated population of tolerogenic dendritic cells according to the invention are utilized to induce tolerance to tolerogen of interest, e.g. donor antigens present in transplantation, autoantigens, and the like. The tolerogen may be presented by pulsing the dendritic cells with the tolerogenic molecule, by targeting the tolerogen to immunosuppressive DCs using anti-CCR9, anti-CMKLR-1 or anti-CD103 specific antibodies or alternatively the CCR9-, CMKLR-1- or CD103 ligands CCL25 (or TECK; Thymus-Expressed ChemoKine), Chemerin or E-Cadherin respectively, by introducing the dendritic cells to a host mammal in a combined formulation of the dendritic cells of the invention and a tolerogen, by introducing tolerogenic dendritic cells of a donor MHC type, and the like. While the dendritic cells of the invention may be genetically modified, such modification is not required for induction of tolerance. Tolerogenic dendritic cells may also be selected for the expression of markers known to be present on immature pDC populations in the human, such as CMKLR1 (a recently deorphaned chemokine receptor "chemokine-like receptor 1), or on myeloid DC populations such as the integrin alpha-E (CD103).

In some embodiments a substantially pure population of the dendritic cells are used in such methods. The isolated cell populations also find use in screening assays for therapeutic methods and compounds, including methods and compositions relating to induction of tolerance.

BRIEF DESCRIPTION OF THE DRAWINGS

FIG. 7A-C. Lethal GVHD of C57BL/6 recipients induced by BALB/c $CD4^+$ $CD25^-$ effector T cells can be suppressed by co-injected C57BL/6 $CCR9^+$ DCs.

FIG. 8A-B. CCR9 expression found on human pDCs: A. Palatine tonsils were digested for 1-2 h at 37° C. with Collagenase Type IV (500 U/ml; Worthington Biochemical) and DNase I (1 U/ml; Sigma) in protein-free media at final concentrations of 2 mg/ml and 1 U/ml. Epithelial cells and debris were removed by percoll, the interface was collected and washed. B. In vitro cultured DCs were obtained from fresh human bone marrow cells. Bone marrow from 2 donors were diluted 1:2 in protein-free RPMI-1640 media and separated over a 1.077 g/ml ficoll gradient (Sigma). The interface was collected and cultured in IMDM media containing 10% FBS and antibiotics in the presence of 100 ng/ml human Flt3L (R&D Systems, MN) and 50 ng/ml human Thrombopoietin (R&D Systems, MN) for 5-10 days in our initial experiments. Cell suspensions were stained with antibodies to Lin-1-FITC (a cocktail of antibodies to CD3, CD14, CD16, CD19, CD20 and CD56; BD Biosciences, CA); and HLA-DR-PerCP-Cy5-5, CD123-PE-Cy7, CD11c-AF700, CCR9-Pacific Blue, CD80-APC and CD86-PE (R&D systmes, MN). Cells were gated on HLA-DR+Lin-1- cells and subdivided into conventional DCs (CD11c+ CD123-) and pDCs (CD11c- CD123+). The pDC gate was analyzed for the expression of costimulatory ligands CD80 and CD86. The quadrants in A and the red line in B delineate the isotype control.

FIG. 12A-B. Immunosuppressive effect of allogeneic CCR9+ pDCs in colitis.

FIG. 13A-B. Antigen-loaded CCR9+ DCs suppress clinical symptoms of EAE. Sorted CCR9+ and CCR9- pDCs from spleens of flt3L-treated C57BL/6 mice were pulsed in vitro with MOG p35-55 or control OVA (323-339) peptide (50 mM) for 2 hrs prior to i.v. injection (5×106) into B6 recipients. Mice were immunized s.c. with MOG (100 mg) in CFA 7 days after transfer followed by i.v. injection of Pertussis toxin (200 ng) two days later (A). At the peak of disease, 21 days after immunization, splenocytes were cultured (105) with escalating doses of MOG in vitro for 72 hrs followed by a 3H-Thymidine pulse (1 mCi) for 18 hrs (B). Legend applies to both A & B. Error bars represent the SEM for one of two representative experiments.

Figure 1:
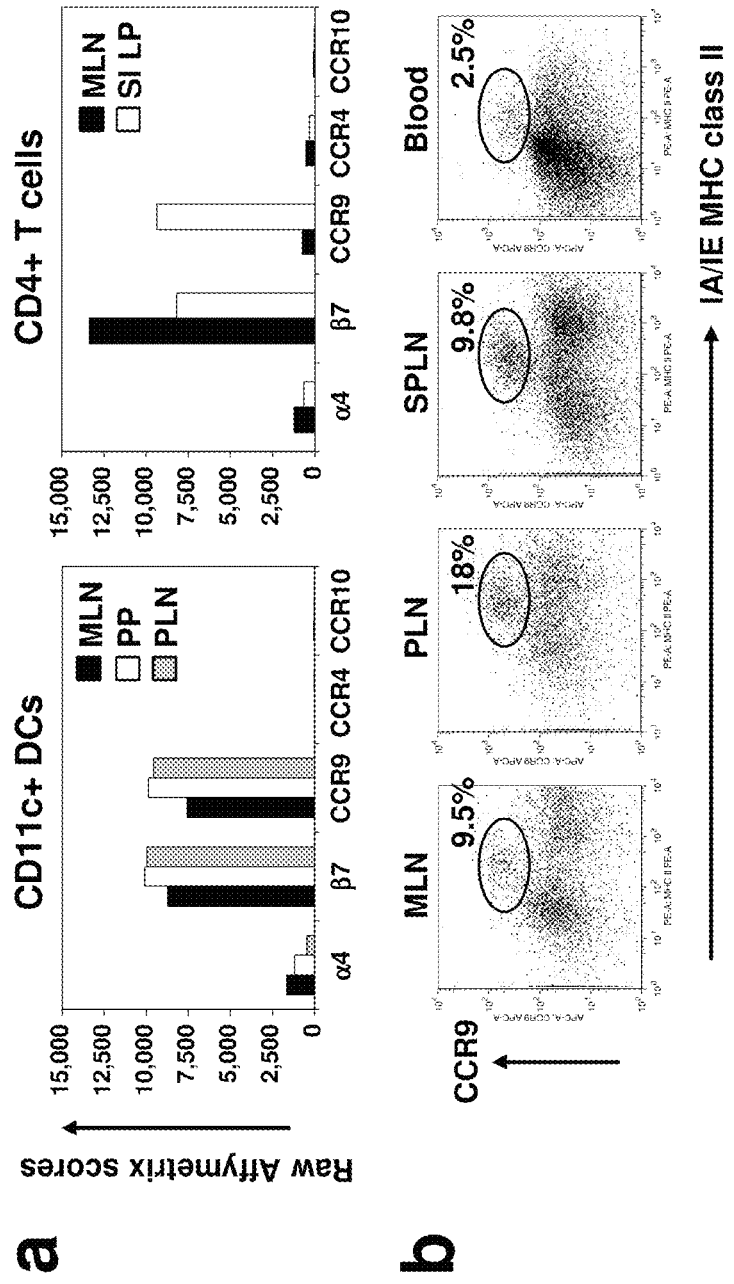
FIG. 1A-B. Tissue-specific CCR9 expression profiles of DCs.

DESCRIPTION OF THE SPECIFIC EMBODIMENTS $CCR9^+$ DCs are typically of the plasmacytoid DC lineage, possess an immature phenotype and rapidly downregulate CCR9 in response to maturation-inducing pDC-restricted Toll-like receptor ligands. $CCR9^+$ pDCs are potent inducers of regulatory T cell function and suppress antigen-specific immune responses both in vitro and in vivo, including inhibition of acute graft-versus-host disease induced by allogeneic $CD4^+$ donor T cells in irradiated recipients. Immature human pDCs also expressed CCR9 and in previous studies the novel recently de-orphaned chemokine receptor CMKLR1 (Zabel et al. (2005). J Immunol 174:244-251).

Here we set forth the isolation of the most potent tolerogenic DCs based on phenotypic markers that define them, which include, without limitation, CCR9 on immature mouse and human pDCs, CMKLR1 on immature human pDCs; CD103 on mouse and human conventional DCs (Jaensson et al. (2008). J Exp Med 205: 2139-2149), and the like.

By segregating cDCs or immature pDCs based on their robust expression of such a phenotypic marker and introducing such cells into a mammalian recipient, 100% survival in GVHD studies was achieved, for example using $CCR9^+$ pDCs or CD103+ cDCs, compared to their respective $CCR9^-$ or CD103- counterparts or no DC transfer at all, which resulted in a vigorous alloimmune response and subsequent wasting. Chemokine receptor CCR9 or the integrin alpha-E are reliable markers for the isolation of tolerogenic immature pDCs or cDCs respectively from in vitro expanded DC populations, or from freshly isolated cell populations. The use of other markers of immature dendritic cells, e.g. costimulatory ligands, such as CD40, CD80, and CD86, as negative selection markers is undesirable due to the potential immunostimulatory effect of antibody-mediated cross-linking of these ligands on DCs.

The isolation of tolerance-inducing DCs can provide immense therapeutic benefits in clinical adoptive immunotherapy for autoimmune disorders or to induce transplant tolerance. The success of animal studies shown herein can be applied to the clinic, where the tolerogenic CCR9+, CD103+ or CMKLR-1+ human DC can be expanded, sorted by flow cytometry and used to induce transplant tolerance or loaded with autoantigens to target autoimmune diseases. The methods may further be practiced in conjunction with the expansion of dendritic cells in vivo, for example through administration of Flt3-L, GM-CSF, and the like.

In solid organ transplants, the immune system of recipients can be tolerized initially to donor alloantigens by introducing tolerogenic DCs mobilized from bone marrow of donors prior to tissue engraftment. In bone marrow transplants, donor bone marrow may be tolerized to recipient alloantigens by introducing tolerogenic DCs expanded from bone marrow of recipients, together with the donor transplant.

The tolerogen of interest may be delivered to peripheral tissues, e.g. skin, muscle, etc. or other localized sites, e.g. lymph nodes, Peyer's patches, etc., and may be given as a combined formulation with dendritic cells of the invention, or as separate formulations. The tolerogen may also be added to a DC population prior to administration, e.g. to a freshly isolated cell population, an in vitro culture of expanded DCs, etc. The methods of the invention are particularly useful in situations where the host response to an antigen is undesirable, for example in conditions of autoimmune diseases, prior to transplantation, prior to xenotransplantation, and the like.

Mammalian species that may benefit from specific reduction of immune responses include canines; felines; equines; bovines; ovines; etc. and primates, particularly humans. Animal models, particularly small mammals, e.g. murine, lagomorpha, etc. may be used for experimental investigations. Animal models of interest include those involved with the immune responses to autoantigens, alloantigens, and the like.

Specific tolerance is desirable for ameliorating, limiting, or postponing the onset of an unwanted immune response in a subject. Accordingly, the methods and compositions of this invention are of considerable interest in the treatment of a number of human diseases having an etiology involving an unwanted immune response.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

Dendritic cell. As used herein, the term refers to any member of a diverse population of morphologically similar cell types found in lymphoid or non-lymphoid tissues. Dendritic cells are a class of "professional" antigen presenting cells, and have a high capacity for sensitizing MHC-restricted T cells. Dendritic cells may be recognized by function, or by phenotype, particularly by cell surface phenotype. These cells are characterized by their distinctive morphology, intermediate to high levels of surface MHC-class II expression and ability to present antigen to T cells, particularly to naive T cells (Steinman et al. (1991) Ann. Rev. Immunol. 9:271; incorporated herein by reference for its description of such cells). The dendritic cells affected by the methods of the invention may be selected to be immature or mature dendritic cells.

The cell surface of dendritic cells is unusual, with characteristic veil-like projections, and is characterized by expression of the cell surface markers CD1a+, CD4+, CD86+, or HLA-DR+. Mature dendritic cells are typically CD11c+, while precursors of dendritic cells include those having the phenotype CD11c−, IL-3Rα$^{low}$; and those that are CD11c− IL-3Rα$^{high}$. Treatment with GM-CSF in vivo preferentially expands CD11b$^{high}$, CD11c$^{high}$ DC, while Flt-3 ligand has been shown to expand CD11c$^+$ IL-3R$\alpha^{low}$ DC, and CD11c$^-$ IL-3R$\alpha^{high}$ DC precursors.

Fixed Cell.

The term "fixed" as used herein refers to the practice of adding a chemical compound for preserving cell structure for analysis. A fixed cell remains physically stable for an extended period. Fixed cells are not viable, i.e. they do not replicate or undergo conventional metabolic reactions. However, the antigenic structure of a fixed cell is typically preserved. Preferably the tolerogenic fixed cells of the invention maintain antigen integrity, retention of cellular morphology, and light scatter properties, as measured by current instrumentation, in a reproducible manner over time. Such stability may be tested, for example, by the ability of the cells to maintain, after fixation, reactivity with a variety of well defined antibodies, this number being a minimum of, but not limited to, cluster designation (CD) markers as defined by the Council on Human Leucocyte Differentiation Antigens.

The term "chemically fixed" as used herein is intended to mean fixation of treatment of cells with a chemical, as for example but without limiting the invention, glutaraldehyde, paraformaldehyde, ethanol, formaldehyde, methanol, to create links between proteins, thereby stabilizing the antigenic structure. The particular conditions and apparatus used to fix cells are known in the art. Preferably, the fixed cells are thoroughly rinsed prior to usage to substantially reduce the amount of unreacted fixative within the cells. The number of rinses needed to achieve thorough rinsing is within the skill of the art. Thereafter, the fixed cells are processed immediately or stored in an aqueous environment with or without preservative until processing to prevent drying out and shrinkage of the cells, i. e. to keep the tissue component in a "wet" or hydrated state.

Tolerogen. As used herein, the term "tolerogen" refers to a molecule for which immunologic tolerance is desired, which is typically presented in combination with the dendritic cells described herein in order to induce stable, long-lasting tolerance, e.g. for greater than about one week, greater than about two weeks, greater than about three weeks, greater than about one month, or more.

The practitioner has a number of choices for tolerogenic molecules used in the methods of this invention. The tolerogen contributes to the specificity of the tolerogenic response that is induced. It may or may not be the same as the target antigen, which is the antigen present or to be placed in the subject being treated which is a target for the unwanted immunological response, and for which tolerance is desired.

A tolerogen of this invention may be a polypeptide, polynucleotide, carbohydrate, glycolipid, or other molecule isolated from a biological source, or it may be a chemically synthesized small molecule, polymer, or derivative of a biological material, providing it has the ability to induce tolerance according to this description when combined with the mucosal binding component.

In certain embodiments of this invention, the tolerogen is not in the same form as expressed in the individual being treated, but is a fragment or derivative thereof. Tolerogens of this embodiment include peptides based on a molecule of the appropriate specificity but adapted by fragmentation, residue substitution, labeling, conjugation, and/or fusion with peptides having other functional properties. The adaptation may be performed for any desirable purposes, including but not limited to the elimination of any undesirable property, such as toxicity or immunogenicity; or to enhance any desirable property, such as mucosal binding, mucosal penetration, or stimulation of the tolerogenic arm of the immune response.

Terms such as insulin peptide, collagen peptide, and myelin basic protein peptide, as used herein, refer not only to the intact subunit, but also to allotypic and synthetic variants, fragments, fusion peptides, conjugates, and other derivatives that contain a region that is similar (preferably 70% identical, more preferably 80% identical and even more preferably 90% identical at the amino acid level) to at least 10 and preferably 20 consecutive amino acids of the respective molecule for which it is an analog, wherein the region of the derivative shares with the respective parent molecule an ability to induce tolerance to the target antigen.

Tolerogenic regions of an inducing antigen may be different from immunodominant epitopes for the stimulation of an antibody response. Tolerogenic regions are generally regions that can be presented in particular cellular interactions involving T cells. Tolerogenic regions may be present and capable of inducing tolerance upon presentation of the intact antigen. Some antigens contain cryptic tolerogenic regions, in that the processing and presentation of the native antigen does not normally trigger tolerance.

In certain embodiments of this invention, two, three, or a higher plurality of tolerogens are used. It may be desirable to implement these embodiments when there is a plurality of target antigens. It may also be desirable to provide a cocktail of antigens to cover several possible alternative targets. For example, a cocktail of histocompatibility antigen fragments could be used to tolerize a subject in anticipation of future transplantation with an allograft of unknown phenotype. In another example, a mixture of allergens may serve as inducing antigen for the treatment of atopy.

Tolerogens can be prepared by a number of techniques known in the art, depending on the nature of the molecule. Polynucleotide, polypeptide, and carbohydrate antigens can be isolated from cells of the species to be treated in which they are enriched. Short peptides are conveniently prepared by amino acid synthesis. Longer proteins of known sequence can be prepared by synthesizing an encoding sequence or PCR-amplifying an encoding sequence from a natural source or vector, and then expressing the encoding sequence in a suitable bacterial or eukaryotic host cell.

In certain embodiments of this invention, the tolerogen comprises a complex mixture of antigens obtained from a cell or tissue, one or more of which plays the role of tolerogen. The tolerogens may be in the form of whole cells, either intact or treated with a fixative such as formaldehyde, glutaraldehyde, or alcohol; in the form of a cell lysate, created by detergent solubilization or mechanical rupture of cells or tissue, followed by clarification. The tolerogens may also be obtained by subcellular fractionation, particularly an enrichment of plasma membrane by techniques such as differential centrifugation, optionally followed by detergent solubilization and dialysis. Other separation techniques are also suitable, such as affinity or ion exchange chromatography of solubilized membrane proteins.

Mixtures of antigens from cells or tissues are of particular interest in a number of applications of this invention. For example for the treatment of organ-specific autoimmune disease, where the identity of the target antigen is unknown, or to provide a plurality of antigens to heighten the tolerogenic response. Suitable sources of cells for this purpose would be a biopsy sample of the same tissue from the subject to be treated, or a cultured cell line of the same tissue type. To tolerize a recipient to a planned tissue graft, the cell source is preferably obtained from either the donor or an individual sharing at least one major histocompatibility complex allotype with the donor. In humans, preferably two or more allotypes are shared at the HLA-A/B and HLA-DR locus (in order of increasing preference in the treatment of graft rejection; in the order of decreasing preference in the treatment of graft-versus-host disease). For tolerization against histocompatibility class II antigens (the usual target of an acute allograft rejection), peripheral blood mononuclear cells, spleen cells or lymph node cells are particularly appropriate. For tolerization against carbohydrate antigens (the usual target of hyperacute xenograft rejection), it is appropriate to use any cell type that is enriched at the target, such as endothelial cells or leukocytes.

Tolerogenic Dendritic Cell Compositions

For use in the methods of the invention, it is desirable to isolate populations of tolerogenic dendritic cells. Separation by cell staining may use conventional methods, as known in the art, including magnetic bead separation, affinity selection, fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be antibodies, or other specific receptors or ligands for the cell surface molecule CCR9, CMKLR1 or CD103, which are optionally used in combination with reagents specific for one or both of CD11c and B220 in mice (gated on CD3/CD19 negative cells); and Lin-1 (i.e. non-DC lineage markers such as one or more of CD3, CD14, CD16, CD19, CD20, CD56), CD11c and CD123 in humans. The cells may be isolated from lymphoid tissue, from blood, or from in vitro culture, e.g. bone marrow culture, etc. In addition to antibody reagents, polynucleotide probes specific for an mRNA of interest, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to cells, and incubated for a period of time sufficient to bind the available antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The cells of interest may be separated from a complex mixture of cells by techniques that enrich for cells having the above described characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for tolerogenic dendritic cells are achieved in this manner. The subject population may be at or about 50% or more of the cell composition, and preferably be at or about 75% or more of the cell composition, and may be 90% or more. The desired cells are identified by their surface phenotype, by the ability to induce tolerance, etc. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for tolerogenic dendritic cells may be used in a variety of screening assays and cultures, as described below.

The enriched tolerogenic dendritic cells population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive such as Flt3L and thrombopoietin. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells. Optionally, cofactors such as all-trans retinoic acid to induce CCR9 expression or 1α, 25 dihydroxyvitamin D3 and/or dexamethasone or other steroid-based agents known to be immunosuppressive, are included in expansion culture medium at a concentration sufficient to increase the number of tolerogenic DC populations in in vitro cultures. In addition to, or instead of growth factors, the subject cells may also be grown in a co-culture with fibroblasts, stromal or other feeder layer cells.

Methods of Use

The tolerogenic dendritic cells may find use in methods of inducing tolerance. Various routes and regimens for delivery may be used, as known and practiced in the art. The dose of cells may be from about $10^4$-$10^9$ per dose, depending on the size of the animal and the tolerogen. Administration may be at a localized site, e.g. sub-cutaneous, or systemic, e.g. intraperitoneal, intravenous, etc. Tolerogenic formulations will typically contain from about 0.1 µg to 1000 µg, more preferably 1 µg to 100 µg, of the selected tolerogen, while in embodiments where the dendritic cells are derived from a graft donor, no exogenous tolerogen is required. The tolerogen composition may additionally contain biological buffers, excipients, preservatives, and the like. The dendritic cells may be pulsed with tolerogen prior to administration, e.g. by suspending the dendritic cells in a solution of the tolerogen, followed by washing the cells, prior to administration. If desired, the cells may be administered in several doses, e.g. twice weekly, weekly, monthly, etc., for a period of time sufficient to induce long-term tolerance.

The cells may be administered in any physiologically acceptable medium, normally intravascularly, although they may also be introduced into any convenient site, where the cells may find an appropriate site for tolerization. Usually, at least $1\times10^5$ cells will be administered, preferably $1\times10^6$; $10^7$, $10^8$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with dendritic cell proliferation and differentiation.

Conditions of interest for treatment include preparation for allogeneic transplantation, where the dendritic cells have at least one MHC allele in common with the cells to be transplanted, which MHC allele is normally present in the recipient. For example, a human recipient that is matched with a tissue, organ or cell at 4 out of 5 HLA A, B and C alleles may be tolerized with dendritic cells that bear the two unmatched alleles. In this way the recipient is made tolerant of all HLA alleles present in the engrafted cells.

Allogeneic (i.e. mismatched at one or more MHC alleles) tolerogenic DC populations may be used in suppression of Inflammatory Bowel Disease (IBD). IBD includes a number of debilitating disorders such as ulcerative colitis or Crohn's disease that affects millions of people especially in industrialized societies. Mismatched immunosuppressive DCs of the invention, i.e. dendritic cells differing in at least one MHC locus from the recipient, can induce the development of a large percentage of immunosuppressive regulatory T cells in vivo and in vitro. Up to two thirds of recently activated CD4+ CD25+ T cells express foxp3 after incubation with allogeneic tolerizing pDCs in vitro. IBD is usually targeted to gut flora which contains a wide heterogenous mixture of enteric bacteria and antigens. Broad induction of immunosuppressive T cells in the gut tissues, aided by the gut-homing capacity of these DC populations (in particular CCR9 and alpha-E) to reach gut T cells, suppress IBD, as demonstrated in the well-established immunodeficient SCID transfer model of colitis, which is controlled by defined CD4+ T cell subsets.

The subject cells may be used in a wide variety of ways. The nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

The cells may be used in conjunction with a culture system in the isolation and evaluation of factors associated with the differentiation and maturation of dendritic cells. Thus, the cells may be used in assays to determine the activity of media, such as conditioned media, evaluate fluids for growth factor activity, involvement with dedication of lineages, or the like.

Genes may be introduced into the dendritic cells for a variety of purposes, e.g. replace genes having a loss of function mutation, provide recognition of a particular antigen, suppress activation of a particular antigen receptor, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into target mammalian cells are available. The vectors may be episomal, e.g. plasmids, virus derived vectors such as cytomegalovirus, adenovirus, etc., or may be integrated into the target cell genome, through homologous recombination or random integration, e.g. retrovirus derived vectors such MMLV, HIV-1, ALV, etc. Retrovirus based vectors have been shown to be particularly useful when the target cells are hematopoietic progenitor cells. For example, see Schwarzenberger et al. (1996) Blood 87:472-478; Nolta et al. (1996) P.N.A.S. 93:2414-2419; and Maze et al. (1996) P.N.A.S. 93:206-210.

To prove that one has genetically modified cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of tolerization, maturation, etc. while maintaining the ability to express the introduced DNA. Various tests in vitro and in vivo may be employed to ensure that the capability of the cells has been maintained.

One method interest is the examination of gene expression in the cells of the invention. The expressed set of genes may be compared between the dendritic cell subsets, or against other hematopoietic subsets as known in the art.

Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., *Science* (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system; a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Screening Assays

Tolerizing dendritic cells are also useful for in vitro assays and screening to detect factors and chemotherapeutic agents that are active on dendritic cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, drugs, etc. the dendritic cell composition, usually a culture comprising dendritic cells, is contacted with the agent of interest, and the effect of the agent assessed by monitoring output parameters, such as expression of markers, cell viability, ability to tolerize an animal, and the like. The cells may be freshly isolated, cultured, genetically altered, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function;

Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51 (3):313-24, for examples.

Kits may be provided, where the kit will comprise staining reagents that are sufficient to differentially identify the tolerizing dendritic cells described herein. A marker combination of interest may include CCR9, and one or both of CD11c and B220, as described herein. The staining reagents are preferably antibodies, and may be detectably labeled. Kits may also include tubes, buffers, etc., and instructions for use.

EXPERIMENTAL

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

Example 1

The chemokine receptor CCR9 is selectively expressed on pDCs of immature phenotype in vivo. CCR9 expression was rapidly downregulated in response to maturational signals and could effectively distinguish endogenous pDCs of immature and mature phenotypes. $CCR9^+$ pDCs constituted a sizeable fraction of the pDC compartment in resting secondary lymphoid tissues; in addition, they are substantially more efficient than $CCR9^-$ pDCs at inducing regulatory T cells and they inhibit antigen-specific immune responses both in vitro and in vivo. Finally, sorted and adoptively transferred $CCR9^+$ (but not $CCR9^-$) pDCs effectively prevent acute GVHD, providing long-term suppression of graft versus host responses in an allogeneic T cell transfer model.

Results

DCs express gut-specific T-cell homing receptors. Using a gene expression profiling approach, we evaluated the expression of tissue specific homing receptor transcripts in DCs from different tissues in an effort to explore the homing patterns of DCs and the impact this might have on tissue-specific immune responses. We characterized expression of selected trafficking receptor transcripts in $CD11c^+$ DCs from mesenteric lymph nodes (MLNs), Peyer's patches and peripheral lymph nodes (PLNs); and in memory $CD4^+$ T cells from MLNs and the lamina propria of the small intestine for comparison. We focused on the expression of key gut and skin-specific homing receptors. The expression of gut-selective homing receptors CCR9 and the $\beta_7$ integrin (part of the $\alpha_4\beta_7$ heterodimer) was high among gut-associated T cells, whereas their expression of skin-homing receptors CCR4 and CCR10 was low, validating the assay.

We were surprised however to find high expression levels of CCR9 transcript and protein on DCs from lymphoid tissues, including lymph nodes that drain the gut (MLNs) but also those that do not (PLNs) (FIG. 1). In contrast, transcripts for the skin-homing associated chemokine receptors CCR4 and CCR10 were low in all of the DCs tested here. Flow cytometry confirmed high expression of CCR9 protein on immature CD11c+ MHC class $II^{int}$ cells in lymphoid tissues (FIG. 1), whereas only a small percentage of DCs seen in the blood were $CCR9^+$.

Figure 2:
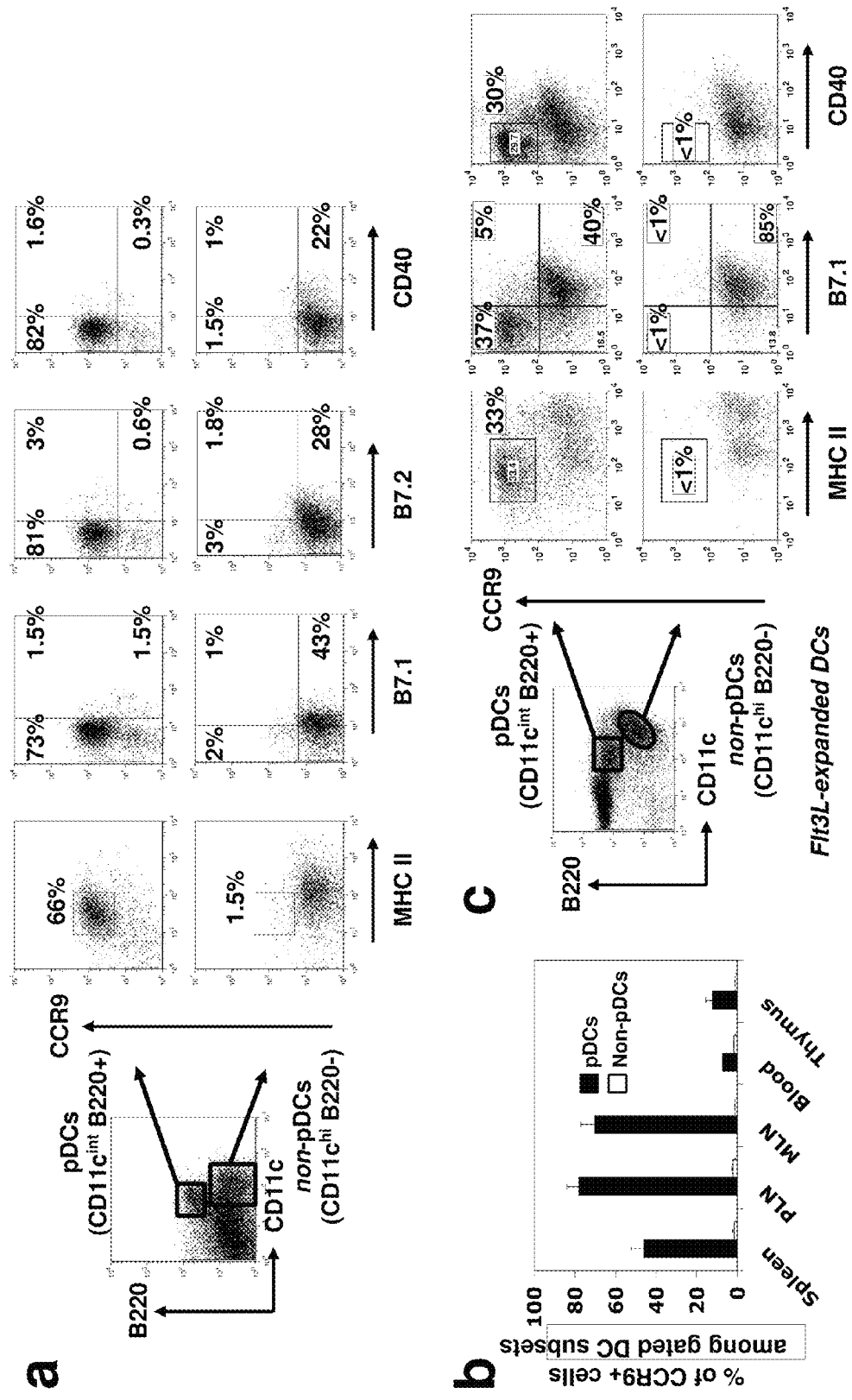
FIG. 2A-C. $CCR9^+$ DCs reside in the plasmacytoid DC compartment and have a predominantly immature phenotype.

CCR9 defines an immature population of plasmacytoid DCs. Using flow cytometry we subdivided the DC populations from different lymphoid tissues into pDCs ($CD11c^{int}B220^+$) and non-pDCs ($CD11c^{hi}B220^-$). The non-pDC group includes $CD11c^{hi}B220^-CD8\alpha^-CD11b^{hi}$ mDCs and so called $CD11c^{hi}B220^-CD8\alpha^{hi}CD11b^{lo}$ "lymphoid" DCs. Almost all of the $CCR9^+$ DCs in the lymphoid tissues examined resided in the pDC subset (FIG. 2a); and almost all displayed an "immature" phenotype as shown by their low expression of costimulatory molecules CD80, CD86 and CD40, and intermediate expression of MHC class II molecules (FIG. 2a). The predominantly CCR9-deficient mDC (non-pDC) compartment contained DCs with slightly higher expression of costimulatory molecules (FIG. 2a bottom). The pDC compartment in lymphoid tissues contained a sizeable population of $CCR9^+$ pDCs (FIG. 2b), with the highest percentage (~70-80%) of pDCs expressing CCR9 in the PLNs and MLNs. The lowest proportion of $CCR9^+$ DCs among pDCs was in the blood and thymus.

As a whole, pDCs are less abundant than mDCs, so that $CCR9^+$ pDCs represent ~12-18% of total $CD11c^+$ DCs in PLNs, ~5-10% of DCs in MLNs and spleen, 2-3% of DCs in blood and <1% in the thymus. To determine whether additional expansion of pDCs in vivo would alter expression of CCR9 on these cells, we transplanted C57BL/6 mice with a B16 melanoma cell line secreting Flt3L (subsequently referred to as Flt3L-treated B6 mice). This system allows us to expand the pDC population without activation, as Flt3L has been shown to be an important growth and differentiation factor for the development of pDCs from hematopoietic stem cells in mice. Flt3L treatment in vivo increased the frequency and number of pDCs in lymphoid tissues by almost 10-fold after 10-14 days. In addition to the $CCR9^+$ pDC population, a distinct population of $CCR9^-$ pDCs was seen with increased expression of costimulatory molecules (FIG. 2c). However, most $CCR9^+$ pDCs remained phenotypically immature even after in vivo expansion with Flt3L. Taken together, the results show that CCR9 defines an immature population of pDCs in peripheral lymphoid tissues, distinguished from most mature pDCs and from mDCs.

$CCR9_+$ pDCs migrate to CCL25. We next asked whether CCR9 on pDCs was functional by assessing the chemotactic responses of different DC subsets to the CCR9 ligand CCL25 (a chemokine formerly called thymus-expressed chemokine or TECK). Because the number of pDCs that can be recovered from normal lymphoid tissues is limiting, we expanded the DC population in Flt3L-treated B6 mice as described above and examined the migration of pooled peripheral lymph node cells in response to various chemokines across a Transwell membrane. As expected, pDCs migrated more efficiently than other DC populations towards CXCL12 (also known as SDF-1, ligand for CXCR4), previously identified as a potent chemoattractant for pDCs (FIG. 3a).

Figure 3:
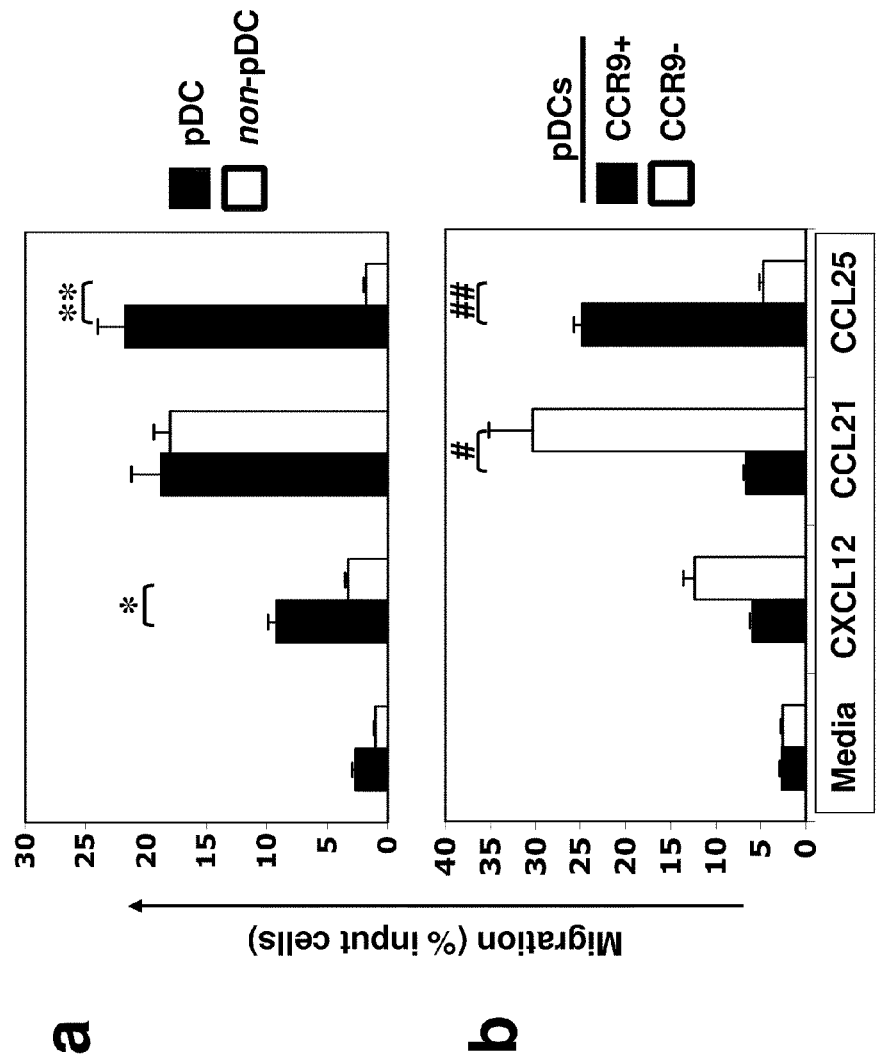
FIG. 3A-B. CCR9 expression allows pDC migration to CCL25.

Interestingly, pDCs were the only DC subset to migrate efficiently in response to CCL25, and with a higher chemotactic response compared to CXCL12 (FIG. 3a). Between $CCR9^+$ and $CCR9^-$ pDC subsets, only the $CCR9^+$ pDC subset migrated efficiently to CCL25 (FIG. 3b). In contrast, consistent with their immature status, $CCR9^+$ pDCs did not migrate to CCL21 (SLC) (FIG. 3b), a ligand for CCR7 that is upregulated on mature DCs upon activation.

Figure 4:
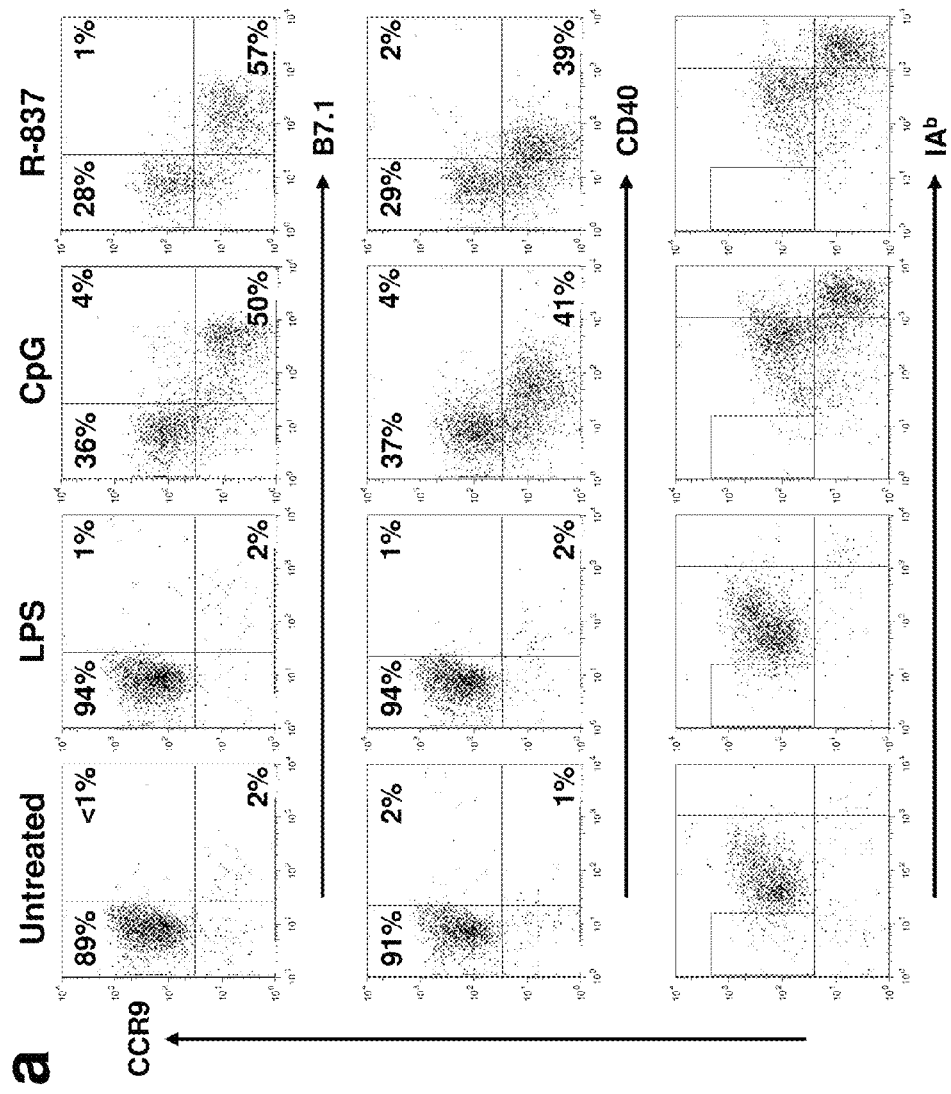
FIG. 4. $CCR9^+$ DCs downregulate CCR9 after activation with pDC-specific TLR ligands.

Activated pDCs produce type I interferon and downregulate CCR9. To determine if CCR9 expression is confined to immature pDCs, or instead is maintained on the $CCR9^+$ subset during maturation, we stimulated in vitro sorted $CCR9^+$ pDCs from Flt3Ltreated B6 mice using an array of Toll-like receptor (TLR) ligands. Unlike mDCs, pDCs do not express TLR2, TLR4, TLR5 or TLR3, making them unresponsive to bacterial products such as peptidoglycans, lipopolysaccharide (LPS) and flagellin or viral double-stranded RNA mimics, respectively. However pDCs are equipped with microbial sensors such as TLR7 or TLR9 that detect the presence of single-stranded RNA or microbial DNA, respectively. As expected, activation of sorted $CCR9^+$ pDCs with LPS induced no DC activation (FIG. 4a) or cytokine production (FIG. 4b), with production of interferon-$\alpha$ (IFN-$\alpha$) and tumor necrosis factor (TNF-$\alpha$) as well as expression of MHC class II and costimulatory molecules CD80 and CD40 remaining low and comparable to untreated cells (FIG. 4).

However, treatment with pDC-specific TLR ligands R-837 (synthetic TLR7 ligand) or bacterial CpG oligonucleotides (TLR9 ligand) downregulated CCR9 on half or more of the cells, with a concomitant increase in MHC class II, CD80 and CD40 expression on the CCR9-downregulated population (FIG. 4a). In addition, overnight treatment with CpG resulted in a burst of IFN-$\alpha$ and TNF-$\alpha$ production by both $CCR9^+$ and $CCR9^-$ pDC subsets (FIG. 4b). These results further support the plasmacytoid identity of CCR9-expressing DCs and define CCR9 as a marker for immature pDCs because CCR9 expression is lost upon TLR-dependent activation of these cells.

Figure 5:
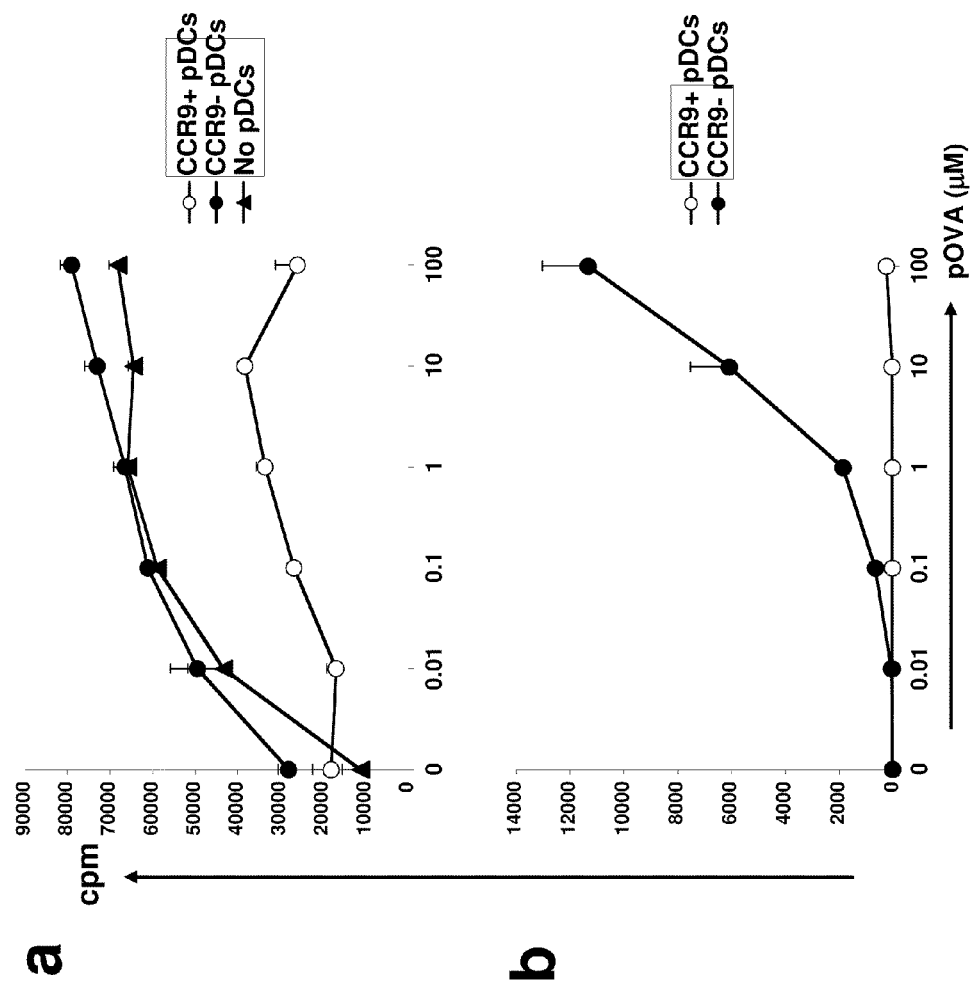
FIG. 5A-B. $CCR9^+$ DCs suppress immune responses in vivo and in vitro.

CCR9+ DCs suppress immune responses and induce regulatory T cells. We next sought to determine whether CCR9+ pDCs, with a characteristic immature phenotype, are potent in suppressing immune responses in vitro and in vivo. Using an antigen specific approach, CCR9+ and CCR9− pDCs were sorted from Flt3L-treated B6 mice and cultured for 2-4 hours with ovalbumin peptide 323-339 (pOVA) prior to i.v. injection into naive B6 mice. Recipient mice were boosted one week later with similar antigen-loaded pDCs and immunized one week after the final boost with pOVA in complete Freund's adjuvant (CFA). After 10 days, draining lymph nodes were examined for in vitro recall responses to pOVA. Lymphoid populations from mice that initially received CCR9+ pDCs were impaired in their ability to proliferate to pOVA in vitro compared with those mice that had received CCR9− pDCs or no pDCs at all (FIG. 5a).

Figure 6:
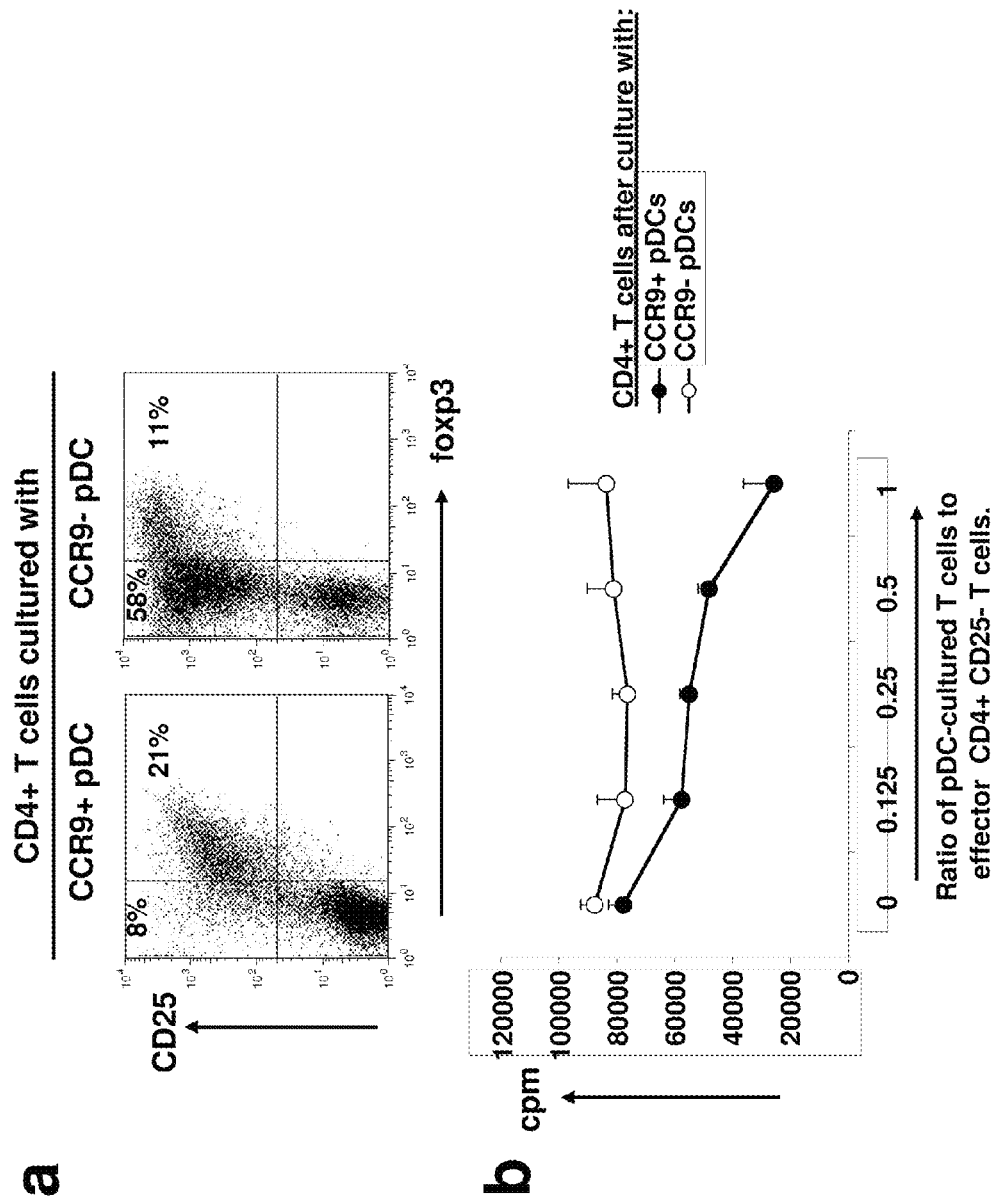
FIG. 6A-B. $CCR9^+$ pDCs are potent inducers of regulatory T cells in vitro.

Since pDCs have been shown to play an important role in inducing distinct CD4+ T helper phenotypes, we wanted to examine the role of CCR9+ DCs in priming T cell responses. We used an in vitro allogeneic stimulation system in which we primed splenic CD4+ T cells from BALB/c mice with sorted CCR9+ and CCR9− pDC subsets from pooled peripheral lymph nodes of Flt3L-treated B6 mice. CCR9+ pDCs failed to support the proliferation of allogeneic T cells (FIG. 5b), in contrast to their CCR9− counterparts. Phenotypic analysis of the cultured T cells showed that CCR9+ pDCs induced fewer activated Foxp3− CD4+ CD25+ T cells than CCR9− pDCs (FIG. 6a). Instead, a higher percentage and a predominant population of Foxp3+ CD4+ CD25+ T cells, which phenotypically resemble regulatory T cells, appeared after 5 days in culture with CCR9+ pDCs compared to cultures with CCR9− pDCs (FIG. 6a). In addition, the CCR9+ pDC-induced T cells suppressed the proliferation of freshly isolated CD4+ CD25− effector T cells in co-culture experiments, whereas T cells primed by the CCR9− DC subset were inefficient at suppressing effector T cell responses (FIG. 6b).

Taken together, these data demonstrate that the CCR9+ pDC population is the major pDC subset that contributes to T cell tolerance, since these cells induce regulatory T cells, exhibit an immature phenotype and represent almost the entire immature pDC pool in lymphoid tissues.

Figure 7A:
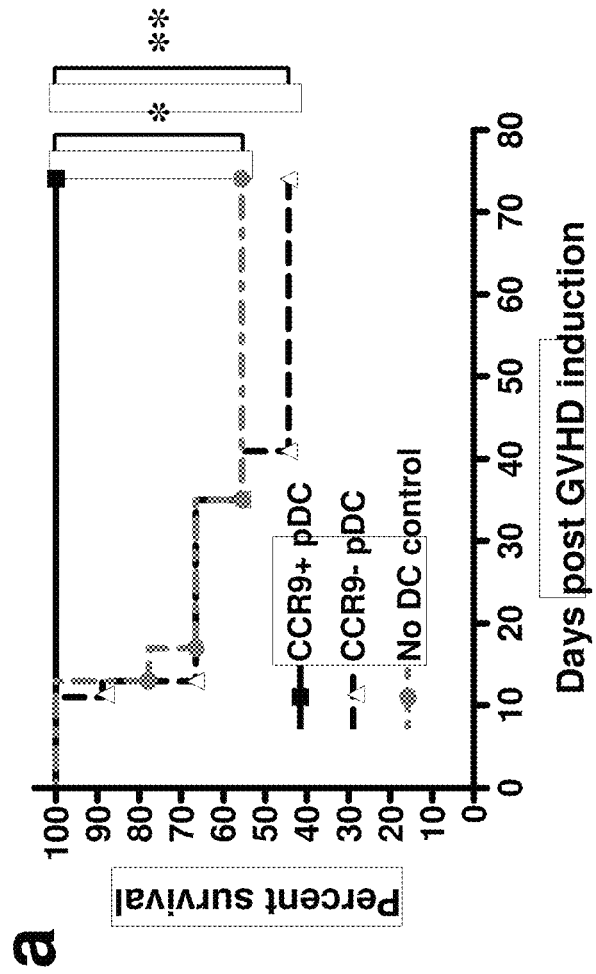

CCR9+ DCs suppress acute GVHD. Since CCR9+ pDCs suppress alloresponses in vitro we wanted to examine the effect of CCR9+ DCs in vivo using an animal model of GVHD induced by allogeneic bone marrow transplantation. To determine whether CCR9+ pDCs from Flt3L-treated B6 mice could suppress GVHD induced by CD4+ CD25− BALB/c T cells, we co-injected the two populations at a 1:2 ratio of DCs to T cells along with T-cell depleted BALB/c bone marrow into C57BL/6 hosts within 24 h after lethal total body irradiation (900 rads). All mice that received CD4+ CD25− effector T cells and bone marrow developed clinical signs of GVHD including diarrhea, skin ulcerations and weight loss; approximately 50% died after 5 weeks (FIG. 7a). Comparable results were seen with mice that received CCR9− pDCs together with CD4+ CD25− effector T cells. The addition of CCR9+ pDCs with effector T cells in bone marrow transplanted hosts rescued all the mice from death (100% in two separate experiments: FIG. 7a) and improved clinical symptoms including diarrhea, weight loss and hunched posture.

To monitor the effects of CCR9+ DCs on coinjected effector T cells, CD4+ CD25− effector T cells were obtained from congenic BALB/c.Thy1.1 mice. All other mice (that is, irradiated recipients and donor mice for the sorted DC subsets and bone marrow) were Thy1.2+. Three weeks after transfer, Thy1.1+ CD4+ effector T cells from PLNs produced substantial amounts of IL-17 and IFN-γ in GVHD mice that received no pDCs (FIG. 7b) compared to unmanipulated healthy controls (percentages of IL-17- and IFN-γ-producing T cells were <1% in PLNs of untreated controls). Co-injection of CCR9+ pDCs suppressed the frequency of IL-17-producing effector T cells by at least 4-fold, without substantially reducing IFN-γ-producing effector cells (FIG. 7b, left).

Since recent studies suggest that the development of $T_H$-17 (IL-17-producing) and $T_H$1 (IFN-γ-producing) cells are antagonistic to each other, co-injected CCR9− pDCs suppressed the appearance of IFN-γ- but not IL-17-producing effector T cells (FIG. 7b, left). IL-17 production in the spleen was less pronounced, but we still observe few IL-17- and many IFN-γ-producing splenic effector T cells after co-transfer of CCR9+ pDCs (FIG. 7b, right). The frequency of cytokine-producing effector T cells was higher in the PLNs and spleen (FIG. 7b) compared to the MLNs. Examination of Thy1.1+ CD4+ effector T cells for the regulatory T cell marker Foxp3, revealed an expansion of Foxp3+ CD25− T cells in the MLNs and spleen of recipient mice that received CCR9+ pDCs (FIG. 7c). In contrast, CCR9− pDCs failed to induce Foxp3+ effector T cells similar to the GVHD controls that did not receive DCs.

Taken together these results show that CCR9+ DCs are potent suppressors of in vivo alloresponses; reducing the clinical severity of allogeneic GVHD, suppressing effector T cell responses (in particular IL-17 production) and inducing de novo development of Foxp3+ regulatory T cells from effector cells.

We have shown that the chemokine receptor CCR9 selectively marks immature pDCs, and that these CCR9+ pDCs are normally present as a resident pDC population in resting secondary lymphoid tissues. CCR9+ DCs underwent maturation by upregulating costimulatory and MHC class II molecules in response to TLR7 and TLR9 but not TLR4 ligands; moreover they produced IFN-α upon TLR activation, confirming their plasmacytoid lineage. Importantly, CCR9 expression was lost upon activation, implying that CCR9 can be used as a reliable marker for immature pDCs. Moreover, we find that the CCR9+, but not CCR9− pDCs potently inhibited immune responses in vivo using an antigen-driven immunization model and an acute GVHD animal model induced by allogeneic bone marrow transplantation.

Immune suppression by CCR9+ DCs involved the inhibition of T cell proliferation and inflammatory cytokine production, presumably reflecting the preferential ability of CCR9+ pDC to induce Foxp3+ regulatory T cells. The findings demonstrate that CCR9 expression defines a physiologically important tolerogenic DC subset, well positioned in lymphoid tissues to participate in homeostatic immune regulation.

CCR9 expression on pDCs permits their chemotaxis to the CCR9 ligand CCL25, as shown here and in a previous study. The two principal cell types that express abundant CCL25 in vivo are the small intestinal epithelium and thymic epithelium. CCR9 mediates migration of intestinal memory T cells and IgA plasma cells to the small intestines, and of T cell precursors to the thymus. Thus, CCR9 may allow tolerogenic DCs to migrate either to the thymus or the gut where they can present peripheral antigens and induce T cell tolerance. Since CCR9 was rapidly downregulated by pDC-specific TLR ligands, activation of CCR9+ pDCs by infectious agents would eliminate their thymic- or gut-specific homing capabilities. CCR9 has recently been implicated in pDC localization to the gut wall, although the present findings imply a more widespread distribution and function of CCR9+ pDCs.

Previous work has suggested that resting DCs have the capacity to sample tissue specific antigens and carry them into the thymus where they induce clonal deletion of antigen specific T cells. The present studies in GVHD, however rule out central tolerance as an important mechanism of GVHD suppression. Thymic generation of regulatory T cells might play a role, but seems unlikely in the timeframe required for suppression of the acute graft-versus-host response. Taken together, these findings rule out the importance of thymic mechanisms in the tolerogenicity of CCR9+ DCs in our model. Rather our data are more consistent with a mechanism involving CCR9+ pDC-induced development of Foxp3+ regulatory T cells from the mature peripheral T cell pool.

A notable finding in our studies was the long-term suppression of disseminated GVHD by CCR9+ DCs. Previous studies have shown that lethal GVHD is initiated predominantly by alloreactive CD4+ donor T cells, but that disease can be inhibited by the co-transfer of CD4+CD25+ regulatory T cells of donor origin. These regulatory T cells have to recognize alloantigens of the recipient in order to mediate their protective effects. In our studies transferred donor CCR9+ DCs are potent inducers of allogeneic Foxp3+ regulatory T cells both in vitro and in vivo. We also see suppressed T cell proliferation in vitro and an altered ratio of IL-17 to IFN-γ production by effector T cells in vivo. In summary, our data suggest that donor T cell recognition of host alloantigens on CCR9+ DCs induces regulatory T cells that inhibit the accumulation of IL-17-producing effector T cells and thereby contribute to potent and prolonged disease suppression.

In contrast to earlier studies, by segregating immature pDCs based on their robust CCR9 expression, we achieved 100% survival of irradiated hosts after transfer of these cells with allogeneic bone marrow- and effector T cells. Transfer of CCR9− pDCs instead, or no pDC transfer at all, resulted in a vigorous alloimmune response and subsequent wasting due to the graft versus host response in the majority of mice.

In conclusion, we have used phenotypic criteria, in particular CCR9 expression, to segregate in vivo-derived tolerogenic pDCs from other DCs; and have shown that this purified subset was remarkably effective at suppressing GVHD. The phenotypic characterization and isolation of tolerance-inducing DC subsets may be of therapeutic benefit in adoptive immunotherapy against a wide range of inflammatory disorders, including autoimmunity, allergic disorders and transplantation.

Methods

Mice. C57BL/6 (CD45.2), congenic CD45.1 (B6.SJL-Ptprc$_a$ Pep3$^b$/BoyJ) and BALB/cJ mice were purchased from the Jackson Laboratory. BALB/C.Thy1.1 congenic mice were bred in the VMU facility of the Veterans Affairs Palo Alto Health Care Systems (VAPAHCS). Mice were housed under specific pathogen-free conditions and were used according to the guidelines set forth by the animal committee of the VAPAHCS.

Flow Cytometric Analysis. Samples were first incubated with the 2.4.G2 anti-Fc receptor antibody (BD Biosciences) for the DC studies to prevent non-specific mAb binding. The following mAbs were used for staining: B220-PerCP (RA3-6B2), CD11c-PE (HL3), CD3-PECy7 (145-2C11), CD19-PECy7 (1D3), IA/IE-biotin (2G9), IA$_b$-FITC (AF6-120.1) CD25-APC (PC61), CD4-PE (RM4-5), CD4-PerC Cy5.5 (RM4-5), Thy1.1-biotin (OX-7) and CD3-PerCP-Cy5.5 (145-2C11) from BD Biosciences and CD40-FITC (HM40-3), CD80-FITC (16-10A1) and CD86-FITC (GL1) from eBioscience. CCR9-APC (242503) was purchased from R&D Systems and used according to the manufacturer's recommendations. Secondary reagents for the visualization of biotinylated mAbs included Streptavidin-Pacific Blue (Invitrogen).

DC isolation and sorting. DCs were isolated from lymphoid tissues of normal C57BL/6 and BALB/c mice using Collagenase IV (Worthington Biochemical Corp) and DNase I (Sigma) in protein-free media at a final concentration of 2 mg/ml and 1 U/ml for 1-2 h at 37° C. Tissues were resuspended and passed over a wire mesh, washed, enumerated and stained with conjugated mAbs. For the isolation of Flt3L-expanded DCs, C57BL/6 mice were injected subcutaneously with $5 \times 10^6$ Flt3L-secreting B16 melanoma cells that promote the expansion of DCs in vivo. After 14 days designated lymph nodes were isolated and passed through a 70-micron nylon mesh. For sorting pure populations of CCR9+ and CCR9− pDCs, the cells were first enriched using CD11c microbeads (Miltenyi) followed by sorting Lin− (CD3− CD19−) CD11c$^{int}$ B220+ cells based on their CCR9 expression.

Chemotaxis. Assays. Pooled lymph node cell suspensions from C57BL/6 mice transplanted with Flt3L-secreting B16 melanoma cells, were resuspended in 100 µl of complete RPMI-1640 medium and loaded into collagen-coated Transwells (Corning 3421; 5 µl µm pore size) that were placed in 24-well plates containing 600 µl medium or medium supplemented with 250-500 nM of CCL25, 100 nM CCL21, or 50 nM CXCL12 (R&D Systems). After 2 h of incubation at 37° C., a constant number of Polystyrene beads (Polysciences, Inc.) were added to each sample to control for recovery of cells from different wells. The migrated cells were collected, counted, and stained with mAb to determine the number of migrated pDC and mDC by flow cytometry. The ratio of the number of pDC that migrated in the presence of chemokine vs. the number of cells that migrated to control media was calculated and is given as the percentage of migrated cells relative to the input.

DC stimulation with TLR ligands. $0.2\text{-}0.5 \times 10^6$ MACS-purified and CCR9 sorted pDCs from pooled peripheral lymph nodes of Flt3L-treated B6 mice were cultured in 200 µl of complete RPMI 1640 medium supplemented with 10% FCS for 8-12 h in the absence or presence of LPS (1 ng/ml), R848 (10 µg/ml) and ODN1826 CpG (1 µM) (Invivogen). Following stimulation, DCs were stained for their expression of MHC class II (IA/IE) and CD80, CD86 or CD40.

Intracellular Foxp3 and cytokine assays. Single cell suspensions of lymph node cells and RBC-free splenocytes were stimulated in vitro at 37° C. for 4 h with 5 ng/ml of Phorbol Myristate Acetate (PMA) (Sigma) and 1 µg/ml of ionomycin (Sigma). Brefeldin A (eBioscience) was added 2 h after the addition of PMAionomycin to a final concentration of 1 µg/ml. Cells were harvested, and stained for surface CD4-PerCPCy5.5 and Thy1.1-biotin followed by the secondary reagent Streptavidin-Pacific Blue (Invitrogen). For the visualization of Foxp3, cells were not stimulated. Following surface staining, cells were washed, fixed and permeabilized according to the manufacturer's recommendation (eBioscience). Cells were then stained in permeabilization buffer (eBioscience) with fluorochrome labeled mAbs for: IFN-γ-FITC (XMG1.2) (eBioscience), IL-17-PE (TC11-18H10) (BD Bioscience,) and IL-10-APC (JES5-16E3) (BD Bioscience) or Foxp3-FITC (FJK-16s) (eBioscience) for the visualization of regulatory T cells. Cells were washed in permeabilization buffer and resuspended in staining buffer for analysis on the flow cytometer. Supernatants from overnight (16 h) pDC cultures stimulated with TLR ligands were examined for the presence of IFN-α using a standardized kit (PBL Biomedical Laboratories) or TNF-α using Luminex Bead Technology with a standardized kit (Millipore).

In vitro T cell stimulation and suppressor T cell assays. $CD4^+$ T cells were enriched from spleens of BALB/c mice using the $CD4^+$ T cell isolation kit (Miltenyi) and cultured with $CCR9^+$ and CCR9– pDCs, sorted from pooled lymph nodes of Flt3L-treated B6 mice, at a 5:1 ratio. To determine T cell proliferation, cultures were setup in 96-well flat-bottom microtiter plates using $2\times10^5$ sorted T cells and $0.4\times10^5$ DCs and stimulated with a dose range of pOVA for 3 days prior to the addition of $_3$H-thymidine (1 μCi/well). After a further 18 h, cultures were harvested and $_3$H-thymidine incorporation measured using a liquid scintillation γ-counter (Wallac). Results are expressed as mean cpm of triplicate cultures. For T cell suppression assays, cultures were setup using larger numbers of sorted T cells ($5\times10^6$) and DCs ($10^6$) for 5-7 days. Aliquots of T cells were analyzed for CD25 and Foxp3 expression as previously described. The remaining cells were cocultured with $CD4_+CD25_-$ effector T cells isolated from spleens of BALB/c mice by negative selection over LD columns (Miltenyi) using the $CD4^+CD25^+$ regulatory T cell isolation kit (Miltenyi). Cultures were set up for 48 h in 96-well plates coated with anti-CD3 (3 μg/ml, 2C11 clone) (eBioscience) and anti-CD28 (3 μg/ml, 37.51 clone) (eBioscience) prior to the addition of $^3$H-thymidine and subsequent determination of T cell proliferation. Results are expressed as mean cpm of triplicate cultures.

Adoptive transfer assays and immunizations $CCR9^+$ and $CCR9^-$ pDCs were sorted from pooled lymph node cells from Flt3L-treated B6 mice and cultured for 2-4 h with 50 μM of ovalbumin peptide 323-339 (pOVA) prior to i.v. administration ($0.5\times10^6$ DCs/mouse) to naive C57BL/6 mice. Recipient mice were boosted 1 week later with the same Ag-loaded pDCs ($0.5\times10^6$ DCs/mouse) and immunized s.c. one week after the final boost with 20 μg pOVA emulsified in CFA (Sigma). After 10 days, cell suspensions from draining lymph nodes were stimulated with a dose range of pOVA for 72 hrs in 96-well plates at $0.5\times10^6$ LN cells/well prior to the addition of $^3$H-thymidine and subsequent determination of cellular proliferation. Results are expressed as mean cpm of quadruplicate cultures.

GVHD model C57BL/6 hosts were given total body irradiation two times from a $^{131}$Cs source, 4 h apart at 450 rads per dose for a cumulative dose of 900 rads. Irradiated mice were injected with donor cells i.v. within 24 h. All mice received $2\times10^6$ T-cell depleted (TCD) bone marrow with $0.5$-$1\times10^6$ splenic $CD4^+CD25^-$ donor T cells both from BALB/c mice. Bone marrow T cells were depleted using anti-Thy1.2 microbeads followed by negative selection through LD columns (Miltenyi). $CD4^+CD25^-$ effector T cells were enriched using the $CD4^+CD25^+$ regulatory T cell isolation kit (Miltenyi) by purifying total $CD4^+$ T cells, followed by negative selection of $CD4^+CD25^+$ T cells through LD columns (Miltenyi). MACS bead enrichment of $CD4^+CD25^-$ T cells and TCD bone marrow resulted in >99% elimination of potential $CD4^+CD25^+$ regulatory and $CD3^+$ effector T cells respectively. Designated groups received in addition to T cells and bone marrow, $0.2$-$0.5\times10^6$ sorted $CCR9^+$ or CCR9– pDCs from pooled lymph nodes of Flt3L-treated B6 mice. In studies involving the analysis of effector T cells post-transfer, $CD4^+CD25^-$ effector T cells were isolated from BALB/c.Thy1.1 congenic mice. Mice were kept on antibiotic water for the first month. The survival and appearance of mice were monitored daily and body weight was measured weekly. For the analysis of effector T cell responses in vivo, mice were evaluated at d10, d20 and d30 for cytokine production and regulatory T cell induction in lymphoid tissues.

Statistical Analysis Data are presented as mean values±standard error of the mean (SEM) unless otherwise indicated. Statistical significance between sets of data was assessed using the two-tailed unpaired Student's t-test for comparison of two groups. Significance between survival curves of different groups in the GVHD studies were assessed using the log rank test. P-values <0.05 were considered statistically significant.

Example 2

Figure 9:
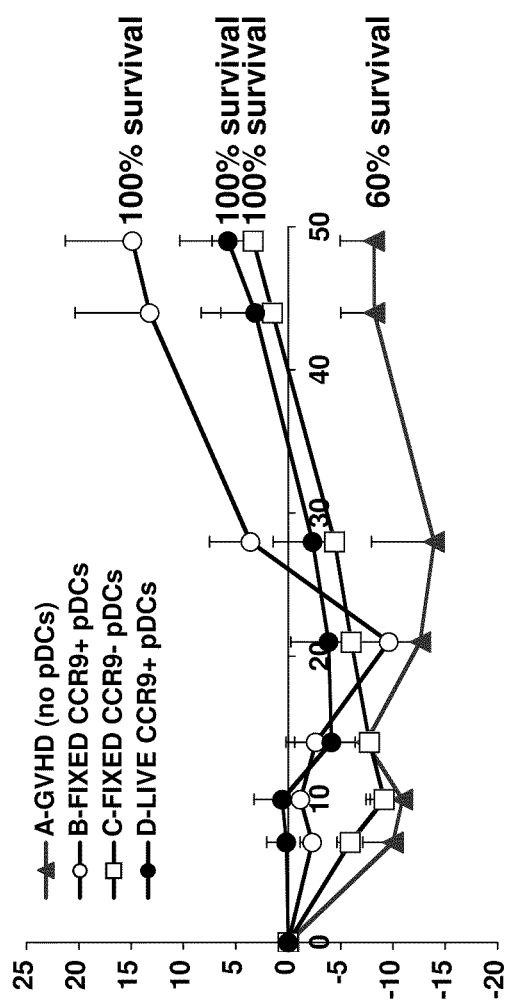
FIG. 9. Immunosuppressive effect of CD103+ cDCs in GVHD.

As shown in FIG. 9, the lethal GVHD of C57BL/6 recipients induced by BALB/c CD4+ CD25– effector T cells can be suppressed by co-injected C57BL/6 CD103+ cDCs. (A) C57BL/6 mice received 2×500 rads of total body irradiation, 5×106 BALB/c T-cell depleted bone marrow cells and 2.5×106 BALB/c splenic CD4+CD25– T cells. Three cohorts of mice received either coinjected sorted CD103+ cDCs, CD103– cDCs or no DCs at all (no DC control) at 0.5-1×106 DCs/mouse from pooled peripheral lymph nodes of flt3L/B16-treated B6 mice. Conventional DCs were sorted based on their expression of CD11c (CD11chigh) but lack of expression of B220 and lineage markers (CD3, CD19 and NK1.1). Representative data from two independent experiments with 5 animals per group are shown. (B) Splenic CD4+ BALB/c T cells (2×105) were cultured for 6 days with sorted CD103+ or CD103– mDCs (1×105 cells) from pooled lymph nodes isolated from flt3L/B16-treated B6 mice. Cytokine expression levels (in pg/ml) determined by sandwich ELISA. Results shown as mean±sem of triplicates.

Figure 10:
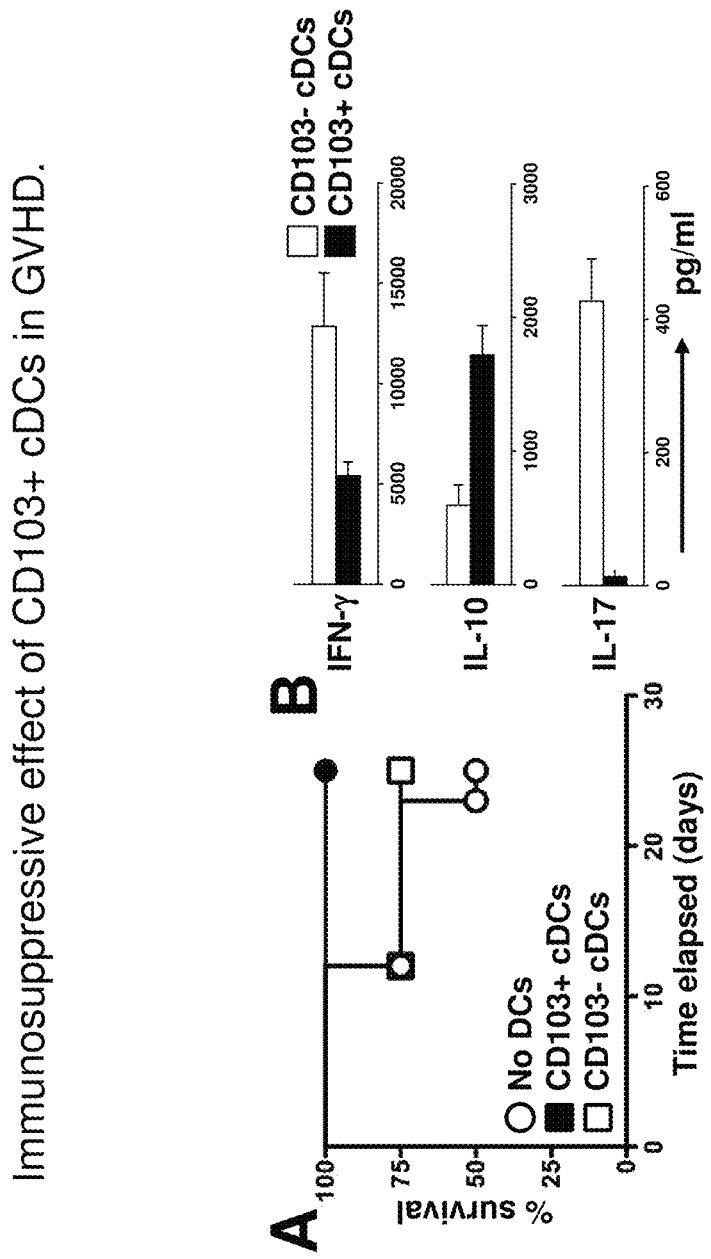
FIG. 10A-B. Immunosuppressive effect of fixed pDC populations in GVHD.

As shown in FIG. 10, lethal GVHD of C57BL/6 recipients induced by BALB/c CD4+ CD25– effector T cells can be suppressed by co-injected FIXED C57BL/6 CCR9+ or CCR9– DCs. (A) C57BL/6 mice received 2×500 rads of total body irradiation, 2.5×106 BALB/c T-cell depleted bone marrow cells and 2.5×106 BALB/c splenic CD4+CD25– T cells. Four cohorts of mice received either no DCs (GVHD control) or coinjected, sorted and fixed CCR9+ pDCs or CCR9– pDCs or as a control, LIVE CCR9+ pDCs at 0.5-1×106 DCs/mouse from pooled peripheral lymph nodes of flt3L/B16-treated B6 mice. Plasmacytoid DCs (pDCs) were sorted based on their intermediate expression of CD11c (CD11cint), high expression of B220 but lack of expression of lineage markers (CD3, CD19 and NK1.1). DCs were fixed for 30 mins in 4% paraformaldehyde and then thoroughly washed in saline. Representative data from two independent experiments with 5 animals per group are shown.

Figure 11:
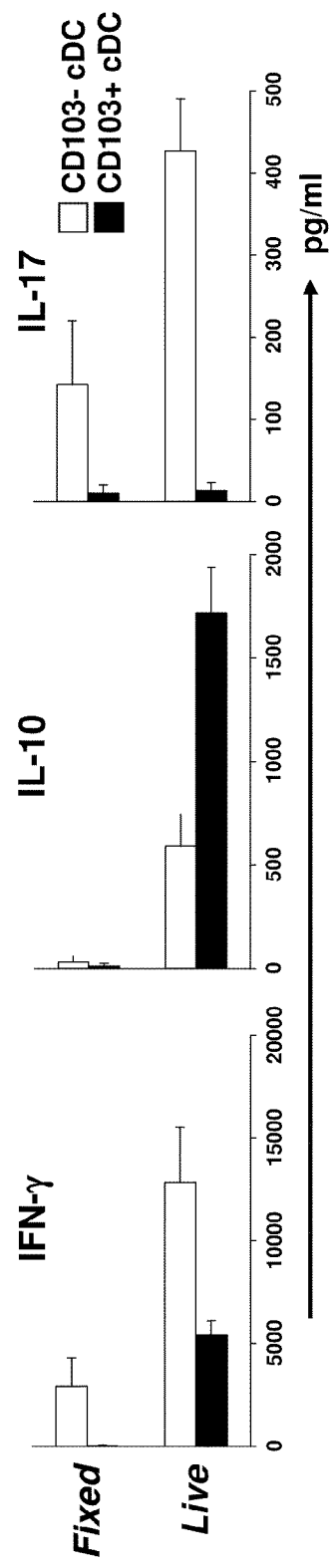
FIG. 11. Immunosuppressive effect of fixed cDC populations on T cell responses in vitro.

As shown in FIG. 11, cytokine release from T cells can be suppressed after culture with fixed cDC subsets whether their live counterparts are tolerogenic (CD103+ subset) or immunostimulatory (CD103– subset). Splenic CD4+ BALB/c T cells (2×105) were cultured for 6 days with either sorted live or fixed CD103+ or CD103– cDCs (1×105 cells) from pooled lymph nodes isolated from flt3L/B16-treated B6 mice. Conventional DCs were sorted based on their expression of CD11c (CD11 chigh) but lack of expression of B220 and lineage markers (CD3, CD19 and NK1.1). DCs were fixed for 30 mins in 4% paraformaldehyde and then thoroughly washed in saline. Cytokine expression levels (in pg/ml) determined by sandwich ELISA. Results shown as mean±sem of triplicates.

As shown in FIG. 12, allogeneic CCR9+ pDCs suppress colitis more efficiently than their CCR9– counterpart. Sorted CCR9+ or CCR9– pDCs (0.5-1×106) from pooled lymph nodes of flt3L/B16-treated B6 mice were co-injected i.v. into SCID mice with sorted 5×105 CD4+ CD45RBhigh T cells from spleens of BALB/c mice. Cohorts of mice that received DCs were boosted with the same population and number of 2 additional DC injections (at 3-4 day intervals). Plasmacytoid DCs (pDCs) were sorted based on their intermediate expression of CD11c (CD11cint), high expression of B220 but lack of expression of lineage markers (CD3, CD19 and NK1.1). Positive control for disease induction included CD4+ CD45RBhigh effector T cell transfer alone into SCIDs; whereas a no disease control included the co-transfer of CD4+ CD45RBhigh effector T cells with sorted CD4+ CD25+ regulatory T cells (1×105) from the spleens of the same BALB/c mice. Error bars represent the SEM of percent weight change (A). % survival of mice in the different cohorts shown in (B). Representative results from two experiments.

As shown in FIG. 13, antigen-loaded CCR9+ DCs suppress experimental autoimmune encephalomyelitis (EAE) in adoptive transfer studies. Multiple sclerosis (MS) is a chronic CNS inflammatory disorder involving demyelination of neuronal axons. Experimental autoimmune encephalomyelitis is a frequently used animal model of human MS in which mice are immunized with myelin self-proteins or peptides in the presence of a potent inflammatory adjuvant containing mycobacterium. We examined the tolerogenic potential of syngeneic antigen-loaded CCR9+ DCs in an antigen-driven model of autoimmunity such as EAE. Sorted splenic pDC subsets (CCR9+ & CCR9−) isolated from flt3L-treated mice were pulsed in vitro with the myelin peptide MOG p35-55 (peptide derived from the myelin oligodendrocyte protein) or control OVA323-339 peptide (peptide derived from chicken ovalbumin) for 2 hours prior to i.v. injection into B6 recipients. Mice were then immunized with MOG peptide in CFA (Complete freund's adjuvant), 7 days after transfer. Control mice that received OVA-loaded DCs or no DCs at all developed clinical symptoms of EAE by day 7 post immunization (A). The transfer of MOG-loaded DCs lowered clinical scores, with the biggest effect achieved by the CCR9+ subset (over 2 fold decrease from OVA loaded DC controls). Proliferation of splenocytes in response to MOG, isolated 3 weeks post immunization, showed a suppressive role of only the MOG-loaded CCR9+ DC subset after adoptive transfer, in support of our clinical findings (B). Therefore syngeneic immunosuppressive DCs can also induce tolerance in antigen-driven autoimmune diseases, if the DC population is pre-incubated with the autoantigen or its peptide All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of decreasing the immune response in a human host to an antigen of interest, the method comprising:
    combining antibodies that specifically recognize CCR9, antibodies that recognize CD11c, and antibodies that recognize CD123 with a sample comprising human plasmacytoid dendritic cells;
    selecting for those cells that are positive for expression of CCR9 and are CD11c⁻ CD123⁺, to provide a tolerogenic dendritic cell population;
    pulsing the tolerogenic dendritic cells with an antigen of interest;
    administering the tolerogenic dendritic cell population in a dose effective to substantially decrease the immune response to the antigen of interest.

2. The method of claim 1, wherein the tolerogenic dendritic cells are chemically fixed.

3. The method according to claim 1, wherein the tolerogenic dendritic cells have been expanded in in vitro culture.

4. The method of claim 3, wherein the tolerogenic dendritic cells are expanded with at least one of Flt3L, GM-CSF, IL-4 and thrombopoietin.

5. The method of claim 4, wherein the cells are expanded in the further presence of at least one of all-trans retinoic acid, 1α, 25 dihydrovitamin D3; and immunosuppressive pharmacologic agents.

* * * * *